US005840491A

United States Patent [19]
Kakizuka

[11] Patent Number: 5,840,491
[45] Date of Patent: Nov. 24, 1998

[54] DNA SEQUENCE ENCODING THE MACHADO-JOSEPH DISEASE GENE AND USES THEREOF

[76] Inventor: Akira Kakizuka, Kyoto University Faculty Housing, #224, Gokasho, Kan'yuchi, Uji-shi, Kyoto, Japan

[21] Appl. No.: 531,927

[22] Filed: Sep. 21, 1995

[30] Foreign Application Priority Data

Sep. 21, 1994 [JP] Japan .................................. 6-251600

[51] Int. Cl.⁶ .............................. C12Q 1/68; C12P 19/34; C07H 21/04
[52] U.S. Cl. ........................... 435/6; 435/91.2; 435/91.5; 435/91.51; 435/810; 536/24.3; 536/24.33; 935/8; 935/77; 935/78
[58] Field of Search ................................ 435/6, 7.1, 91.2, 435/91.5, 810, 91.51; 536/23.1, 24.3, 24.33; 935/6, 8, 17, 77, 78

[56] References Cited

U.S. PATENT DOCUMENTS 5,200,313  4/1993  Corrico ........................................ 435/6

FOREIGN PATENT DOCUMENTS

WO 94/10344  5/1994  WIPO .

OTHER PUBLICATIONS

Takiyama, Y. et al., "The Gene for Machado–Joseph Disease Maps to Human Chromosome 14q," *Nature Genetics*, 4:300–304 (1993).
Kawakami, H. et al., "Unique Features of the CAG Repeats in Machado–Joseph Disease," *Nature Genetics*, 9:344–345 (1995).
Kawaguchi, Y. et al., "CAG Expansions in a Novel Gene for Machado–Joseph Disease at Chromosome 14q32.1," *Nature Genetics*, 8:221–228 (1994).

Karp, S.J. et al., "Molecular Cloning and Chromosomal Localization of the Key Subunit of the Human N–Methyl–D–Aspartate Receptor," *J. Biol. Chem.*, 268(5):3728–3733 (1993).
Maruyama, H. et al., "Molecular Features of the CAG Repeats and Clinical Manifestation of Machado–Joseph Disease," *Human Molecular Genetics*, 4(5):807–812 (1995).
St. George–Hyslop, P. et al., "Machado–Joseph Disease in Pedigrees of Azorean Descent is Linked to Chromosome 14," *Am. J. Human Genetics*, 55:120–125 (1994).
Schöls, L., et al., "Trinucleotide expansion within the MJD1 gene Presents Clinically as Spinocerebellar Ataxia and Occurs Most Frequently in German SCA Patients," *Human Molecular Genetics*, 4(6):1001–1005 (1995).
Ranum, L.P.W., et al., "Spinocerebellar Ataxia Type 1 and Machado–Joseph Disease: Incidence of CAG Expansions Among Adult–Onset Ataxia Patients from 311 Families With Dominant, Recessive or Sporadic Ataxia," *Am. J. Hum. Gen.*, 57:603–608 (1995).
Cancel, G., et al., "Marked Phenotypic Heterogeneity Associated with Expansion of a CAG Repeat Sequence at the Spinocerebellar Ataxia 3/Machado–Joseph Disease Locus," *Am. J. Hum. Gen.*, 57:809–816 (1995).

(List continued on next page.)

*Primary Examiner*—W. Gary Jones
*Assistant Examiner*—Debra Shoemaker
*Attorney, Agent, or Firm*—Hamilton, Brook, Smith & Reynolds, P.C.

[57] ABSTRACT

A method by which a nucleotide sequence, specifically a CAG triplet repeat shown to be expanded in individuals with Machado-Joseph Disease can be identified in a sample obtainable from an individual. The present methods can be used to identify individuals in whom the CAT triplet repeat is expanded, including methods useful to identify the protein encoded by the Machado-Joseph Disease gene.

30 Claims, 8 Drawing Sheets

```
cttttaataccagtgactactttgattcgtgaaacaatgtatttccttatgaatagttttctcatggtgtatttattctttt
         ─────────────────▶
              MJD52
```

```
                                                                         G
aagttttgttttttaaatatacttcacttttgaatgtttcagACAGCAGCAA AAG CAG CAA CAGCAGCAGCAGCAGCAGCAGCA
```

```
                    G
GCAGCAGCAGCAGCAGCAGCGGGACCTATCAGGACAGAGTTCACATCCATGTGAAAGGCCAGCCACCAGTTCAGGAGC
                                         ◀─────────────
                                              MJD25
```

```
ACTTGGAAGTGATCTAGGTAAGGCCTGCTCACCATTCATCATGTTCGCTACCTTCACACTTTATCTGACATAA
◀─────────────
```

OTHER PUBLICATIONS

Takylama, Y., et al., "Evidence for Inter–Generational Instability in the CAG Repeat in the MJD1 Gene and for Conserved Haplotypes at Flanking Markers Amongst Japanese and Caucasian Subjects with Machado–Joseph Disease," *Human Molecular Genetics*, 4(67):1137–1146 (1995).

St. George–Hyslop, P., et al., "Machado–Joseph Disease in Pedigrees of Azorean Descent is Linked to Chromosome 14," *Am. J. Hum. Gen.*, 55:120–125 (1994).

Adams et al. ed.s. The Biochemistry of the Nucleic Acids. Chapman & Hall, new York (1992) pp. 14–19.

Maciel et al. Am. J. Hum. Gen. 57:54–61 (Jul. 1995).

|  |  | TC  | GGC | GTG | GGG | GCC | GTT | GGC | TCC | AGA | CAA | ATA | AAC | 35 |
|  | ATG GAG TCC ATC TTC CAC | GAG | AAA | CAA | GAA | GGC | TCA | CTT | TGT | GCT | CAA | CAT | TGC | 89 |
| 1 | Met Glu Ser Ile Phe His | Glu | Lys | Gln | Glu | Gly | Ser | Leu | Cys | Ala | Gln | His | Cys |  |

```
         TC  GGC GTG GGG GCC GTT GGC TCC AGA CAA ATA AAC           35
    ATG GAG TCC ATC TTC CAC GAG AAA CAA GAA GGC TCA CTT TGT GCT CAA CAT TGC   89
1   Met Glu Ser Ile Phe His Glu Lys Gln Glu Gly Ser Leu Cys Ala Gln His Cys

CTG AAT AAC TTA TTG CAA GGA GAA TAT TTT AGC CCT GTG GAA TTA TCC TCA ATT  143
19  Leu Asn Asn Leu Leu Gln Gly Glu Tyr Phe Ser Pro Val Glu Leu Ser Ser Ile

GCA CAT CAG CTG GAT GAG GAG GAG AGG ATG AGA ATG GCA GAA GGA GGA GTT ACT  197
37  Ala His Gln Leu Asp Glu Glu Glu Arg Met Arg Met Ala Glu Gly Gly Val Thr

AGT GAA GAT TAT CGC ACG TTT TTA CAG CAG CCT TCT GGA AAT ATG GAT GAC AGT  251
55  Ser Glu Asp Tyr Arg Thr Phe Leu Gln Gln Pro Ser Gly Asn Met Asp Asp Ser

GGT TTT TTC TCT ATT CAG|GTT ATA AGC AAT GCC TTG AAA GTT TGG GGT TTA GAA  305
73  Gly Phe Phe Ser Ile Gln Val Ile Ser Asn Ala Leu Lys Val Trp Gly Leu Glu

CTA ATC CTG TTC AAC AGT CCA GAG TAT CAG AGG CTC AGG ATC GAT CCT AT|AAAT  359
91  Leu Ile Leu Phe Asn Ser Pro Glu Tyr Gln Arg Leu Arg Ile Asp Pro Ile Asn

GAA AGA TCA TTT ATA TGC AAT TAT AAG GAA CAC TGG TTT ACA GTT AGA AAA TTA  413
109 Glu Arg Ser Phe Ile Cys Asn Tyr Lys Glu His Trp Phe Thr Val Arg Lys Leu

GGA AAA CAG TGG TTT AAC TTG AAT TCT CTC TTG ACG GGT CCA GAA TTA ATA TCA  467
127 Gly Lys Gln Trp Phe Asn Leu Asn Ser Leu Leu Thr Gly Pro Glu Leu Ile Ser

GAT ACA TAT CTT GCA CTT TTC TTG GCT CAA TTA CAA CAG GAA GGT TAT TCT ATA  521
145 Asp Thr Tyr Leu Ala Leu Phe Leu Ala Gln Leu Gln Gln Glu Gly Tyr Ser Ile

TTT GTT GTT AAG GGT GAT CTG CCA GAT TGC GAA GCT GAC CAA CTC CTG CAG ATG  575
163 Phe Val Val Lys Gly Asp Leu Pro Asp Cys Glu Ala Asp Gln Leu Leu Gln Met

ATT AGG GTC CAA CAG ATG CAT CGA CCA AAA CTT ATT GGA GAA GAA TTA GCA CAA  629
181 Ile Arg Val Gln Gln Met His Arg Pro Lys Leu Ile Gly Glu Glu Leu Ala Gln

CTA AAA GAG CAA AGA GTC CAT AAA ACA GAC CTG GAA CGA ATG TTA GAA GCA AAT  682
199 Leu Lys Glu Gln Arg Val His Lys Thr Asp Leu Glu Arg Met Leu Glu Ala Asn

GAT GGC TCA GGA ATG TTA GAC GAA GAT GAG GAG GAT TTG CAG AGG GCT CTG GCA  737
217 Asp Gly Ser Gly Met Leu Asp Glu Asp Glu Glu Asp Leu Gln Arg Ala Leu Ala

CTA AGT CGC CAA GAA ATT GAC ATG GAA GAT GAG GAA GCA GAT CTC CGC AGG GCT  791
235 Leu Ser Arg Gln Glu Ile Asp Met Glu Asp Glu Glu Ala Asp Leu Arg Arg Ala

ATT CAG CTA AGT ATG CAA GGT AGT TCC AGA AAC ATA TCT CAA GAT ATG ACA CAG  845
253 Ile Gln Leu Ser Met Gln Gly Ser Ser Arg Asn Ile Ser Gln Asp Met Thr Gln

ACA TCA GGT ACA AAT CTT ACT TCA GAA GAG CTT CGG AAG AGA CGA GAA GCC TAC  899
271 Thr Ser Gly Thr Asn Leu Thr Ser Glu Glu Leu Arg Lys Arg Arg Glu Ala Tyr

TTT GAA AA|ACAG CAG |CAA|AAG| CAG |CAA| CAG CAG CAG CAG CAG CAG CAG CAG  953
289 Phe Glu Lys Gln Gln Gln Lys Gln Gln Gln Gln Gln Gln Gln Gln Gln Gln Gln

CAG CAG CAG CAG CAG CAG CAG CAG CAG CAG CGG GAC CTA TCA GGA CAG AGT      1007
307 Gln Gln Gln Gln Gln Gln Gln Gln Gln Gln Arg Asp Leu Ser Gly Gln Ser
```

Figure 1A

```
       TCA CAT CCA TGT GAA AGG CCA GCC ACC AGT TCA GGA GCA CTT GGG AGT GAT CTA    1061
324    Ser His Pro Cys Glu Arg Pro Ala Thr Ser Ser Gly Ala Leu Gly Ser Asp Leu

GGT AAG GCC TGC TCA CCA TTC ATC ATG TTC GCT ACC TTC ACA CTT TAT CTG ACA    1115
342    Gly Lys Ala Cys Ser Pro Phe Ile Met Phe Ala Thr Phe Thr Leu Tyr Leu Thr

TAA GAG CTC CAT GTG ATT TTT GCT TTA CAT TAT TCT TCA TTC CCT CTT TAA TCA    1169
        *
       TAT TAA GAC TCT TAA GTA AAT TTG TAA TCT ACT AAA TTT CCC TGG ATT AAG GAG    1223
       CAA GGT TAC CAA AAA AAA AAA AAA AAA AAG CTA GAT GTG GTG GCT CAC ATC        1277
       TGT AAT CCC AGC ACT TTG GGA AAC CAA GGC AGG AGA GGA TTG CTA GAA CAT TTA    1331
       ATG AAT ACT TTA ACA TAA TAA TTT AAA CTT CAC AGT AAT TTG TAC AGT CTC CAG    1385
       AAA TTC CTT AGA CAT CAT GAA TAT TTT TCT TTT TTT GGG GTG ACA GGG CAA AAC    1493
       TCT GTC TCA AAA AAA AAA AAA AAA AAA GGG CTG GAC ACG GTG GCT TAC GCC        1493
       TGT TAT CCC GGC ACT TTG GGA GGC CAA GGC CGA TGG ATC ACC TGA GGT CAG GAG    1547
       TTC AAG ACC AGC CTG GCC AAC ATG GTG AAA CCC CAT CTC TAC TAA AAA TAC AAA    1601
       AAT TTG CTG GGC ATG GTG GTG GGC ACC TGT AAT CCC AGG AGG CTG AGG CAG GAG    1655
       AAT CAC TTG AAC CTG GGA GCG GAG ATT GCA GTG AGC CAA GAT TGT GCC ATT GAA    1709
       CTC CAG CCT GGG TGA CAA GAC CAA AAC TCC ATC TCA AAA AAA AAA AAA AAA AAA    1763
       GCG ACA GCA ACG G                                                          1776
```

Figure 1B ctttttaataccagtgactactttgattcgtgaaacaatgtatttcccttatgaatagtttttctcatggtgtattattcttttt

→ MJD52 aagttttgttttttaaatatacttcactttttgaatgttcagACAGCAGCAA AAG CAG CAA CAGCAGCAGCAGCAGCAGCAGCA
                                                                G
                                          G
GCAGCAGCAGCAGCAGCGACCTATCAGGACAGAGTTCACATCCATGTGAAAGGCCAGCCACCAGTTCAGGAGC

← MJD25

ACTTGGAAGTGATCTAGGTAAGGCCTGCTCACCATTCATCATGTTCGCTACCTTCACACTTTATCTGACATAA

Met Glu Ser Ile Phe His Glu Lys Gln Glu Gly Ser Leu Cys Ala Gln
1               5                   10                  15

His Cys Leu Asn Asn Leu Leu Gln Gly Glu Tyr Phe Ser Pro Val Glu
                20                  25                  30

Leu Ser Ser Ile Ala His Gln Leu Asp Glu Glu Glu Arg Met Arg Met
            35                  40                  45

Ala Glu Gly Gly Val Thr Ser Glu Asp Tyr Arg Thr Phe Leu Gln Gln
        50                  55                  60

Pro Ser Gly Asn Met Asp Asp Ser Gly Phe Phe Ser Ile Gln Val Ile
65                  70                  75                  80

Ser Asn Ala Leu Lys Val Trp Gly Leu Glu Leu Ile Leu Phe Asn Ser
                85                  90                  95

Pro Glu Tyr Gln Arg Leu Arg Ile Asp Pro Ile Asn Glu Arg Ser Phe
                100                 105                 110

Ile Cys Asn Tyr Lys Glu His Trp Phe Thr Val Arg Lys Leu Gly Lys
            115                 120                 125

Gln Trp Phe Asn Leu Asn Ser Leu Leu Thr Gly Pro Glu Leu Ile Ser
        130                 135                 140

Asp Thr Tyr Leu Ala Leu Phe Leu Ala Gln Leu Gln Gln Glu Gly Tyr
145                 150                 155                 160

Ser Ile Phe Val Val Lys Gly Asp Leu Pro Asp Cys Glu Ala Asp Gln
                165                 170                 175

Leu Leu Gln Met Ile Arg Val Gln Gln Met His Arg Pro Lys Leu Ile
                180                 185                 190

Gly Glu Glu Leu Ala Gln Leu Lys Glu Gln Arg Val His Lys Thr Asp
            195                 200                 205

Leu Glu Arg Met Leu Glu Ala Asn Asp Gly Ser Gly Met Leu Asp Glu
        210                 215                 220

Asp Glu Glu Asp Leu Gln Arg Ala Leu Ala Leu Ser Arg Gln Glu Ile
225                 230                 235                 240

Asp Met Glu Asp Glu Glu Ala Asp Leu Arg Arg Ala Ile Gln Leu Ser
                245                 250                 255

Met Gln Gly Ser Ser Arg Asn Ile Ser Gln Asp Met Thr Gln Thr Ser
                260                 265                 270

Gly Thr Asn Leu Thr Ser Glu Glu Leu Arg Lys Arg Arg Glu Ala Tyr
            275                 280                 285

Phe Glu Lys
        290

Figure 3

```
Arg Asp Leu Ser Gly Gln Ser Ser His Pro Cys Glu Arg Pro Ala Thr
 1           5               10              15

Ser Ser Gly Ala Leu Gly Ser Asp Leu Gly Lys Ala Cys Ser Pro Phe
            20              25              30

Ile Met Phe Ala Thr Phe Thr Leu Tyr Leu Thr
            35              40
```

Figure 4

| | | |
|---|---|---|
| ATGGAGTCCA TCTTCCACGA GAAACAAGAA GGCTCACTTT GTGCTCAACA TTGCCTGAAT | 60 |
| AACTTATTGC AAGGAGAATA TTTTAGCCCT GTGGAATTAT CCTCAATTGC ACATCAGCTG | 120 |
| GATGAGGAGG AGAGGATGAG AATGGCAGAA GGAGGAGTTA CTAGTGAAGA TTATCGCACG | 180 |
| TTTTTACAGC AGCCTTCTGG AAATATGGAT GACAGTGGTT TTTTCTCTAT TCAGGTTATA | 240 |
| AGCAATGCCT TGAAAGTTTG GGGTTTAGAA CTAATCCTGT TCAACAGTCC AGAGTATCAG | 300 |
| AGGCTCAGGA TCGATCCTAT AAATGAAAGA TCATTTATAT GCAATTATAA GGAACACTGG | 360 |
| TTTACAGTTA GAAAATTAGG AAAACAGTGG TTTAACTTGA ATTCTCTCTT GACGGGTCCA | 420 |
| GAATTAATAT CAGATACATA TCTTGCACTT TTCTTGGCTC AATTACAACA GGAAGGTTAT | 480 |
| TCTATATTTG TTGTTAAGGG TGATCTGCCA GATTGCGAAG CTGACCAACT CCTGCAGATG | 540 |
| ATTAGGGTCC AACAGATGCA TCGACCAAAA CTTATTGGAG AAGAATTAGC ACAACTAAAA | 600 |
| GAGCAAAGAG TCCATAAAAC AGACCTGGAA CGAATGTGAG AAGCAAATGA TGGCTCAGGA | 660 |
| ATGTTAGACG AAGATGAGGA GGATTTGCAG AGGGCTCTGG CACTAAGTCG CCAAGAAATT | 720 |
| GACATGGAAG ATGAGGAAGC GAATCTCCGC AGGGCTATTC AGCTAAGTAT GCAAGGTAGT | 780 |
| TCCAGAAACA TATCTCAAGA TATGACACAG ACATCAGGTA CAAATCTTAC TTCAGAAGAG | 840 |
| CTTCGGAAGA GACGAGAAGC CTACTTTGAA AAA | 873 |

Figure 5

```
CGGGACCTAT CAGGACAGAG TTCACATCCA TGTGAAAGGC CAGCCACCAG TTCAGGAGCA    60

CTTGGGAGTG ATCTAGGTAA GGCCTGCTCA CCATTCATCA TGTTCGCTAC CTTCACACTT   120

TATCTGACA                                                          129
```

Figure 6

```
GAATTCCGTT GCTGTCGTCG GCGTGGGGGC CGTTGGCTCC AGACAAATAA ACATGGAGTC    60

CATCTTCCAC GAGAAACAAG AAGGCTCACT TTGTGCTCAA CATTGCCTGA ATAACTTATT   120

GCAAGGAGAA TATTTTAGCC CTGTGGAATT ATCCTCAATT GCACATCAGC TGGATGAGGA   180

GGAGAGGATG AGAATGGCAG AAGGAGGAGT TACTAGGGAA GATTATCGCA CGGTGTGACA   240

GCAGCCTTCT GGAAATATGG ATGACAGTGG TTTTTTCTCT ATTCAGGTTA TAAGCAATGC   300

CTTGAAAGTT TGGGGTTTAG AACTAATCCT GTTCAACAGT CCAGAGTATC AGAGGCTTAG   360

GATCGATCCT ATAAATGAAA GATCATTTAT ATGCAATTAT AAGGAACACT GGTTTACAGT   420

TAGAAAATTA GGAAAACAGT GGTTTAACTT GAATTCTCTC TTGACGGGTC CAGAATTAAT   480

ATCAGATACA TATCTTGCAC TTTTCTTGGC TCAATTACAA CAGGAAGGTT ATTCTATATT   540

TGTTGTTAAG GGTGATCTGC CAGATTGCGA AGCTGACCAA CTCCTGCAGA TGATTAGGGT   600

CCAACAGATG CATCGACCAA AACTTATTGG AGAAGAATTA GCACAACTAA AAGAGCAAAG   660

AGGCCATAAA ACAGACCTGG AACGAATGTT AGAAGCAAAT GATGGCTCAG GAATGTTAGA   720

CGAAGATGAG GAGGATTTGC AGAGGGCTCT GGCACTAAGT CGCCAAGAAA TTGACATGGA   780

AGATGAGGAA GCAGATCTCC GCAGGGCTAT TCAGCTAAGT ATGCAAGGTA GTTCCAGAAA   840

CATATCTCAA GATATGACAC AGACATCAGG TACAAATCTT ACTTCAGAAG AGCTTCGGAA   900

GAGACGAGAA GCCTACTTTG AAAAA                                        925
```

Figure 7

```
CGGGACCTAT CAGGACAGAG TTCACATCCA TGTGAAAGGC CAGCCACCAG TTCAGGAGCA        60

CTTGGGAGTG ATCTAGGTAA GGCCTGCTCA CCATTCATCA TGTTCGCTAC CTTCACACTT       120

TATCTGACAT AAGAGCTCCA TGTGATTTTT GCTTTACATT ATTCTTCATT CCCTCTTTAA       180

TCATATTAAG ACTCTTAAGT AAATTTGAAT CTACTAAATT TCCCTGGATT AAGGAGCAAG       240

GGTACCAAAA AAAAAAAAAA AAAAAAAGC TAGATGTGGT GGCTCACATC TGTAATCCCA        300

GCACTTTGGG AAACCAAGGC AGGAGAGGAT TGCTAGAACA TTTAATGAAT ACTTTAACAT       360

AATAATTTAA ACTTCACAGT AATTTGTACA GTCTCCAGAA ATTCCTTAGA CATCATGAAT       420

ATTTTTCTTT TTTTGGGGTG ACAGGGCAAA ACTCTGTCTC AAAAAAAAAA AAAAAAAAA       480

AAGGGCTGGA CACGGTGGCT TACGCCTGTT ATCCCGGCAC TTTGGGAGGC CAAGGCCGAT       540

GGATCACCTG AGGTCAGGAG TTCAAGACCA GCCTGGCCAA CATGGTGAAA CCCCATCTCT       600

ACTAAAAATA CAAAAATTTG CTGGGCATGG TGGTGGGCAC CTGGAATCCC AGGAGGCTGA       660

GGCAGGAGAA TCACTTGAAC CTGGGAGCGG AGATTGCAGT GAGCCAAGAT TGTGCCATTG       720

AACTCCAGCC TGGGTGACAA GACCAAAACT CCATCTCAAA AAAAAAAAA AAAAAGGGG        780

ACAGCAACGG CGACAGCAAC GGAATTC                                          807
```

Figure 8

```
CTTTTAATAC CAGTGACTAC TTTGATTCGT GAAACAATGT ATTTTCCTTA TGAATAGTTT      60
TTCTCCATGG TGTATTTATT CTTTTAAGTT TTGTTTTTTA AATATACTTC ACCTTTTGAA    120
TGTTCAGA                                                              128
```

Figure 9

```
CGGGACCTAT CAGGACAGAG TTCACATCCA TGTGAAAGGC CAGCCACCAG TTCAGGAGCA      60
CTTGGGAGTG ATCTAG                                                      76
```

Figure 10

```
CTTTTAATAC CAGTGACTAC TTTGATTCGT GAAACAATGT ATTTTCCTTA TGAATAGTTT      60
TTCTCCATGG TGTATTTATT CTTTTAAGTT TTGTTTTTTA AATATACTTC ACCTTTTGAA    120
TGTTTCAG                                                              128
```

Figure 11

```
CGGGACCTAT CAGGACAGAG TTCACATCCA TGTGAAAGGC CAGCCACCAG TTCAGGAGCA      60
CTTGGGAGTG ATCTAGGTAA GGCCTGCTCA CCATTCATCA TGTTCGCTAC CTTCACACTT    120
TATCTGACA                                                             130
```

Figure 12

DNA SEQUENCE ENCODING THE MACHADO-JOSEPH DISEASE GENE AND USES THEREOF

RELATED APPLICATION

This application is a Continuation-In-Part of Japanese patent application number H6-251600, filed Sep. 21, 1994, (Title: The protein related to the Human Machado-Joseph Disease, the cDNA and gene that code this protein, the vector that includes this DNA or gene, the host cell that has been transformed by this manifestation vector, and the diagnostic method and treatment medication" by: Akira Kakizuka), the teachings of which are expressly incorporated herein by reference.

BACKGROUND OF THE INVENTION

The Machado-Joseph Disease (hereafter abbreviated as MJD) is one of the disorders of unknown causes, characterized by the degeneration of the nervous system. It was initially known by different names among the clinical medical practices in several countries. In 1976, however, it was revealed that the disorder is a clinical subtype primarily linked to abnormalities in the same gene. After this, it was determined that the abnormality in the gene took the form of a dominant gene with autosomal inheritance. In Japan MJD was reported for the first time in 1983, and ever since then, there has been a steady increase in the reported incidence of this disease.

The age at which patients experience the onset of MJD ranges widely from approximately 10 years to 50 years of age. The initial symptoms most frequently manifested are an alteration in the patient's ability to walk due to impaired balance ataxia, gradually followed by signs of disequilibrium, incoordination of movement, nystagmus, ocular motor apraxia and amyotrophy. Approximately 10 years after the onset of the disease, at an advanced stage, patients become contained to a wheelchair and eventually become bedridden. Machado-Joseph Disease is uniformly fatal. As the generation advances, it has been the trend that the patients experience the onset of this disease at an increasingly young age.

In recent years, it has been the general understanding that the MJD is a disease caused by a single abnormal gene. Accordingly, a great deal of research has been conducted on the gene locus of MJD. In 1993, Tsuji and his group were able to determine that the MJD gene mapped to the human chromosome 14q24.3-32.1. (Takiyama, Y. et al., *Nature Genetics*, 4:300 (1993)). However, they were unable to identify the MJD gene.

SUMMARY OF THE INVENTION

The present invention relates to the identification and characterization of the gene associated with Machado-Joseph Disease located on human chromosome 14, specifically human chromosome 14q32.1. The gene contains a highly polymorphic CAG repeat region which is unstable and expanded in individuals with Machado-Joseph Disease. Analysis of the CAG repeat region demonstrates a direct correlation between the copy number, or size, of the expanded CAG repeat region and the age-of-onset and severity of Machado-Joseph Disease. In normal individuals (i.e., individuals who are not affected by Machado-Joseph Disease, or not at risk of being affected with Machado-Joseph Disease) the gene contains fewer than about 40 trinucleotide repeats, and typically between about 14 and about 34 CAG trinucleotide repeats. Individuals affected with Machado-Joseph Disease, or at risk of being affected with Machado-Joseph Disease show expansion of this CAG repeat region. The CAG repeat region of the Machado-Joseph Disease gene of these individuals contains at least about 60 CAG repeats, typically at least 61 CAG repeats but less than 150 repeats. In general, the copy number of CAG trinucleotide repeats present in individuals affected with Machado-Joseph Disease is expanded to about 60 to about 90, and more specifically from about 61 to about 84.

Specifically, the present invention relates to the DNA sequence of the MJD gene located on human chromosome 14q32.1 comprising SEQ ID NO:1, the complementary strand of SEQ ID NO:1 and DNA/RNA sequences that hybridize to SEQ ID NO:1 under conditions of stringency described herein. The CAG repeat region can optionally contain two variant triplets, CAA and AAG. Typically, the expansion of the CAG repeat occurs on the 3' side of these variant sequences.

The present invention also encompasses oligonucleotides, particularly PCR primers, and hybridization probes useful for diagnosing Machado-Joseph Disease. The oligonucleotides include nucleotide sequences capable of hybridizing to all or a portion of the Machado-Joseph Disease gene, its complementary DNA or Machado-Joseph Disease RNA. The Machado-Joseph Disease gene has a CAG trinucleotide repeat region in which, if an individual is affected with MJD, the CAG repeat region is expanded. The primers or probes of the present invention are sufficiently complementary to a portion of a strand of the Machado-Joseph Disease gene having a CAG repeat region to hybridize to the Machado-Joseph Disease gene sequence. Sufficiently complementary as defined herein means that the oligonucleotide sequence need not reflect e.g., the exact Machado-Joseph Disease gene sequence, but must be sufficiently similar in identity of sequence to hybridize with the MJD gene under moderate or stringent conditions (conditions of stringency are discussed in Ausubel, F. M., et al. *Current Protocols in Molecular Biology* (Current Protocols, 1994)), the teachings of which are incorporated herein by reference. For example, non-complementary bases can be interspersed in SEQ ID NO:1, primer/probe sequences can be shorter or longer than SEQ ID NO:1 provided that the primer/probe has sufficient complementary bases with SEQ ID NO:1 to specifically hybridize therewith. Such primers/probes can comprise as few as about 10 nucleotides in length up to the entire gene sequence.

Also encompassed by the present invention is the protein encoded by the Machado-Joseph Disease gene described herein (SEQ ID NO:2). The protein, also referred to herein as the Machado-Joseph Disease protein, or protein characteristic of, or associated with Machado-Joseph Disease, contains a polyglutamine tract $(Gln)_n$, in which the number of glutamine amino acid residues is expanded in individual affected with Machado-Joseph Disease. For example, at least about 60 glutamine residue repeats are contained in the protein obtained from individuals affected with Machado-Joseph Disease, typically at least 61 Gln residues, but less than 150 residues. In general, the copy number of Gln residues present in individuals affected with Machado-Joseph Disease is about 60 to about 90, and more specifically from about 61 to about 84. The polyglutamine tract can optionally contain two variant amino acids encoded by the codons, CAA (Gln) and AAG (Lys). Typically, the polyglutamine tract occurs on the 3' side of the variant amino acid residues.

The present invention specifically relates to methods of diagnosing Machado-Joseph Disease. In particular, the present invention encompasses methods of predicting whether an individual is likely to be affected by MJD (or predisposed to the development of, or at risk for MJD), or of determining the presence of the abnormal MJD gene in an individual. As defined herein, the abnormal Machado-Joseph Disease gene contains an expanded CAG trinucleotide repeat characteristic of Machado-Joseph Disease. In one embodiment of the present invention a method for the detection of the presence of expanded CAG triplets is provided. The method uses a hybridization probe which hybridizes with all, or a portion of, the DNA sequence of the Machado-Joseph Disease gene (SEQ ID NO:1), its complementary DNA or its RNA.

The primers/probes of the present invention are capable of discriminating between DNA obtained from normal individuals (i.e., individuals not affected with Machado-Joseph Disease or those individuals that do not have an expanded CAG triplet repeat in chromosome 14 DNA) and individuals affected with Machado-Joseph Disease (i.e., individuals that exhibit symptoms characteristic of Machado-Joseph Disease, or those individuals that have an expanded CAG repeat in chromosome 14 DNA). For example, an individual affected with Machado-Joseph Disease will have chromosome 14 DNA that contains an expanded CAG trinucleotide repeat. A nucleic acid probe can be designed to include all, or a portion, of SEQ ID NO: 1 that hybridizes to DNA with an expanded CAG trinucleotide repeat region, that allows for a detection of a change in the size or structure of DNA containing the CAG expansion by electrophoretic means. Thus, the probe would allow for discrimination between normal DNA and abnormal DNA characteristic of Machado-Joseph Disease on the basis of the presence of the expanded repeat region.

The probe can include a $(CAG)_n$ repeat region, or its complement, wherein n is at least about 60. The probe hybridizes with DNA containing an expanded CAG repeat region present in a biological sample obtained from an individual affected with MJD. That is, the probe hybridizes with DNA obtained from human chromosome 14 and allows for determination and a change in the MJD gene's size or strucutre due to the expanded CAG repeat.

The biological sample can be whole blood or a blood cellular component, such as leukocytes. The biological sample can also be tissue taken from, e.g., the brain, spinal cord, heart, muscle and other body organs. Optionally, these samples can be treated with restriction enzymes (i.e., cut with restriction enzymes) to obtain fragments of the chromosome 14 DNA suitable for hybridization.

In other embodiments of the present invention, methods are provided for diagnosing a predisposition to the development of Machado-Joseph Disease, or for detecting the presence of Machado-Joseph Disease in an individual using antibodies that bind to all, or a portion of, the protein encoded by the abnormal Machado-Joseph Disease gene. The protein encoded by the abnormal Machado-Joseph Disease gene contains an expanded polyglutamine tract, i.e., a region of glutamine residues wherein the number of glutamine residues contained in this region is at least about 60. The antibodies of the present invention are capable of binding to SEQ ID NO:2 wherein SEQ ID NO:2 contains an expanded polyglutamine tract. Antibodies useful in the present invention are capable of binding to the MJD protein and allow for determination of a change in the protein size, structure or charge due to the CAG nucleotide repeat expansion.

The protein encoded by the abnormal Machado-Joseph Disease gene contains an expanded glutamine residue region resulting in an abnormal protein of a different size (i.e., larger) than the protein encoded by the normal Machado-Joseph Disease gene (i.e., the normal protein does not contain an expanded glutamine residue region). The protein encoded by the abnormal Machado-Joseph Disease gene can also have structural characteristics that distinguish it from protein encoded by the normal Machado-Joseph Disease gene. For example, due to the expanded glutamine residue region, the abnormal Machado-Joseph Disease protein can have a different three-dimensional conformation than the normal protein, or a different charge (e.g., the abnormal Machado-Joseph Disease protein can be more negatively charged than the normal Machado-Joseph Disease protein). These characteristic differences between abnormal and normal Machado-Joseph Disease protein due to the expanded glutamine residue region can be used to determine the presence of abnormal Machado-Joseph Disease protein in a biological sample. Antibodies that bind to abnormal Machado-Joseph Disease protein can be used in Western analysis to detect the presence of abnormal Machado-Joseph Disease protein.

The structural differences between abnormal and normal Machado-Joseph Disease protein can result in different binding characteristics where, e.g., an antibody will bind to the abnormal Machado-Joseph Disease protein but not to the structurally distinct normal Machado-Joseph Disease protein. Such antibodies can be used in enzyme linked immunosorbant assays (ELISAs) or radioimmunoassays (RIAs).

The charge differences between abnormal and normal Machado-Joseph Disease protein can also result in distinguishing characteristics. For example, charge differences can result in the abnormal Machado-Joseph Disease protein migrating at a different rate than normal protein e.g., a polyacrylamide gel or a size exclusion column. Such charge differences can also be used in ion-exchange chromatographic methods to determine the presence of abnormal Machado-Joseph Disease protein.

For example, a sample of tissue, or body fluid which contains cells (e.g., cerebral spinal fluid or blood) can be obtained from the individual to be tested. The sample can be processed to render the cells suitable for reaction with a labeled antibody that detects abnormal Machado-Joseph Disease protein in the sample. The sample is then contacted with the antibody under conditions suitable for 35 the antibody to detect the abnormal Machado-Joseph Disease protein. The abnormal Machado-Joseph Disease protein is altered by e.g., size, conformation or charge due to the expanded glutamine tract resulting from the CAG expansion. Detection of the abnormal Machado-Joseph Disease protein is an indication of a predisposition to Machado-Joseph Disease or the presence of Machado-Joseph Disease in the individual.

Antibodies of the present invention can also recognize DNA/RNA nucleic acid sequences characteristic of Machado-Joseph Disease. These antibody probes can also be used in the methods of diagnosis described herein. For example, an antibody can be used to detect the presence of DNA from chromosome 14 that contains the expanded CAG triplet repeat characteristic of individuals affected with Machado-Joseph Disease.

In another embodiment of the present invention, PCR techniques can be used to determine whether a CAG repeat is expanded in an individual. Using the oligonucleotides of the present invention as primers, PCR technology can be used in the diagnosis of the Machado-Joseph Disease by detecting a region of expanded CAG repeating trinucleotides contained in DNA obtained from chromosome 14. Generally, this involves treating separate complementary strands of the DNA sequence containing a region of repeating CAG codons with a molar excess of two oligonucleotide primers, extending the primers to form complementary primer extension products which act as templates for synthesizing the desired sequence containing the CAG repeating units, and detecting the sequence so amplified, for example, by electrophoretic means.

The oligonucleotides, or fragments thereof, of the present invention can be used in any combination for sequencing or producing amplified DNA sequences using various PCR techniques for the amplification of the DNA sequence characteristic of Machado-Joseph Disease. As used herein, the term "DNA characteristic of Machado-Joseph Disease" means that the DNA contains an expanded CAG repeat region e.g., a (CAG)n repeat region, wherein n is at least about 60. As used herein, the term "amplified DNA sequence" refers to DNA sequences that are copies of a portion of a DNA sequence and its complementary sequence. The copies correspond in nucleotide sequence to the original MJD sequence and its complementary sequence. The term "complement", as used herein, refers to a DNA sequence that is complementary to a specified DNA sequence. The term "primer pair", as used herein, means a set of primers including a 5' upstream primer that hybridizes with the 5' end of the DNA sequence to be amplified and a 3' downstream primer that hybridizes with the 3' end of the sequence to be amplified.

BRIEF DESCRIPTION OF THE DRAWINGS

FIG. 1 depicts the nucleotide sequence (SEQ ID NO:1) and the deduced amino acid sequence (SEQ ID NO:2) of the human Machado-Joseph Disease DNA isolated from a human brain cDNA library. The CAG repeat is shown in bold type. The variant triplets, CAA and AAG, are boxed. Human Alu repetitive sequences are underlined. The identified exon-intron boundaries are shown by bars.

FIG. 2 depicts the genomic sequence of the Machado-Joseph Disease gene surrounding the CAG repeat region (SEQ ID NO:3). The CAG repeat is shown in bold type. The intron sequence is shown in lower case. The variant triplets, CAA and AAG, are boxed. Primer sequences used for PCR analyses are indicated by arrows. Nucleotide substitutions found in at least two individuals are shown above the genomic sequence.

FIG. 3 depicts a amino acid sequence of the protein characteristic of Machado-Joseph Disease designated SEQ ID NO: 4, also referred to herein as base Sequence B, which is located on the 5' side of the Gln residue.

FIG. 4 depicts an amino acid sequence of the protein characteristic of Machado-Joseph Disease designated SEQ ID NO: 5, also referred to herein as base Sequence A, which is located on the 3' side of the Gln residue repeat region.

FIG. 5 depicts a nucleic acid sequence characteristic of Machado-Joseph Disease designated SEQ ID NO: 6, which is located on the 5' side of the CAG triplet repeat region.

FIG. 6 depicts a nucleic acid sequence characteristic of Machado-Joseph Disease designated SEQ ID NO: 7, which is located on the 3' side of the CAG triplet repeat region.

FIG. 7 depicts a nucleic acid sequence characteristic of Machado-Joseph Disease designated SEQ ID NO: 8, also referred to herein as basic Sequence C, which is located on the 5' side of the CAG triplet repeat region.

FIG. 8 depicts a nucleic acid sequence characteristic of Machado-Joseph Disease designated SEQ ID NO: 9, which is located on the 3' side of the CAG triplet repeat region.

FIG. 9 depicts a nucleic acid sequence characteristic of Machado-Joseph Disease designated SEQ ID NO: 10, which is located on the 5' side of the CAG triplet repeat region.

FIG. 10 depicts a nucleic acid sequence characteristic of Machado-Joseph Disease designated SEQ ID NO: 11, also referred to herein as base Sequence D, which is located on the 3' side of the CAG triplet repeat region.

FIG. 11 depicts a nucleic acid sequence characteristic of Machado-Joseph Disease designated SEQ ID NO: 12, which is located on the 5' side of the CAG triplet repeat region.

FIG. 12 depicts a nucleic acid sequence characteristic of Machado-Joseph Disease designated SEQ ID NO: 13, which is located on the 5' side of the CAG triplet repeat region.

DETAILED DESCRIPTION OF THE INVENTION

The present invention is based on Applicants' identification and characterization of the Machado-Joseph Disease (MJD) gene and the encoded Machado-Joseph Disease protein.

In characterizing the MJD gene Applicant used a probe with a CTG repeat that is complementary to the CAG repeat region and screened a cDNA library prepared from the brain cortex of a normal, healthy person. The cDNA clone CAG-27 was obtained.

With the CAG-27 fragment as a probe, a human genomic library screening was conducted. Positive clones were obtained, and it was further determined that these clones were mapped in the human chromosome 14, specifically at 14q32.1. This increased the possibility that CAG-27 was, indeed, the gene associated with the MJD. When the human brain DNA library was again screened, using the CAG-27 fragment, two new types of clones were obtained. When they were compared, it was found that the splicing site existed immediately before the CAG repeat. Then, using an oligonucleotide from the 3' side of the CAG repeat as a probe, the human genomic library was once again screened. As a result, from the positive clones, the intron structure immediately before the CAG repeat was obtained and the cDNA sequence (SEQ ID NO: 1) and the predicted amino acid sequence (SEQ ID NO: 2) of the Machado-Joseph Disease gene was determined. As shown in FIG. 1, the MJD nucleotide sequence comprises 1776 base pairs (bp) with one long open reading frame. The CAG repeat region contains two variant sequences, CAA and AAG, at three positions and the CAG repeat is predicted to be translated into a polyglutamine tract at the C-terminal portion of the open reading frame. Although the amino acid sequence shows no homology to any previously reported sequence, a homologous nucleotide sequence was identified, in GenBank, as a human X chromosome STS (HUMSWX784). Alu repeat sequences were identified in the 3' noncoding region. Identification of the CAG repeat in a human brain cDNA library shows that the mRNA is expressed in the human brain; this was further confirmed using RT-PCR. Human brain RNA gave rise to two PCR fragments containing the CAG repeats and this amplification was reverse transcriptase-dependent, demonstrating that both alleles of the MJD1 gene are transcribed in the human brain.

PCR (polymerase chain reaction) was successfully conducted by using a primer having a nucleotide sequence located on the the 5' side of the intron and on the 3' side of the CAG repeat (FIG. 2). It was determined from the results of the agarose electrophoresis of the PCR product that whereas normal, healthy persons had a CAG repeat of less than approximately 40 copies and typically 13 to 36 copies, all the patients with MJD had a trinucleotide repeat of at least approximately 60 copies, and typically 61–84 copies of the repeat.

Thus, the present invention encompasses the following:
(1) the protein encoded by MJD gene;
(2) the cDNA that encodes this protein;
(3) the gene that encodes this protein;
(4) an expression vector that includes the cDNA indicated in (2) above or the gene indicated in (3) above;
(5) the host cell that has been transformed by the expression vector indicated in (4) above; and
(6) methods of diagnosis for MJD.

Encompassed by the present invention is the protein characteristic of MJD (SEQ ID NO: 2, also referred to herein as the protein associated with Machado-Joseph Disease) the MJD protein encoded by the MJD gene (SEQ ID NO: 1) and homologues and biologically active fragments thereof. Specifically encompassed is the homologue that contains the amino acid sequence combined with the Arg part of the amino acid sequence (hereafter referred to as amino acid sequence A) indicated in SEQ ID NO: 5 in which the Lys part of the amino acid sequence indicated by SEQ ID NO: 4, that is substantially in pure form, intervenes with $(Gln)_n$ (whereby within the equation, n represents an integer less than 150, and the $(Gln)_n$ region can contain at least one Lys in its sequence.)

The polypeptide that contains the amino acid sequence A (SEQ ID NO:5) that is "substantially in pure form" signifies a polypeptide that contains the amino acid sequence, in which over 90% of the polypeptides at the time of production, for example, 95%, 98% or 99%, are indicated by the amino acid sequence A.

The "polypeptide that contains the amino acid sequence A" signifies not only a polypeptide made of the amino acid sequence A, but also a polypeptide to which is added at the N-terminal end and/or C-terminal end, an alternative polypeptide with 20% (preferably within 5%) of the amount of amino acid of the amino acid sequence A.

The homologue of the polypeptide that contains the amino acid sequence A (SEQ ID NO:5) is a continuous length of amino acid in which the general amino acid length is at least 100, preferably at least 150, that is, 200, 250 or 300 amino acid residues, for example, and the homology is at least 70%, preferably, 80%, more preferably 90% and most preferably over 95%.

The polypeptide fragment that includes the amino acid sequence A (SEQ ID NO:5), or fragments homologous to it, signify a polypeptide or a homologue containing the amino acid sequence A (SEQ ID NO:5), in which the amino acid sequence is at least 10 residues, and preferably at least 15, for example, 20, 25, 30, 40, 50 or even 60 amino acid residues.

The polypeptide homologue that contains the amino acid sequence A (SEQ ID NO:5), its fragments and its homologue are also described herein as lacking a part of their amino acid sequence, in addition to the description that they contain the amino acid sequence combined with the Arg part of the amino acid sequence indicated in SEQ ID NO: 5 n which the Lys part of the amino acid sequence indicated by SEQ ID NO: 4 intervenes with the $(Gln)_n$ (whereby within the equation, n represents an integer less than 150, and the (Gln)n can contain at least one Lys in its sequence) and including fragments and homologues that lack a part of their amino acid sequence, (for example, within a whole protein, a polypeptide that includes only the part necessary for biological activity); others in which one amino acid is replaced with another amino acid, (for example, those replaced by an amino acid with similar characteristics), as well as those in which a different amino acid is added or inserted.

The CAG repeat region can comprise only the CAG repeat itself, or additionally include the CAA and/or AAG, both variants of CAG. According to the present invention, it has been determined that the copy number of the CAG repeat for a normal, healthy person is fewer than about 40, and that for an individual affected with MJD, it is at least about 60. More specifically, the CAG repeat in normals was present from about three to about 36 times, and in affected individuals was from about 60 to about 90 times. Depending on the severity of the disease, it is reasonable that the number could exceed 100. Accordingly, within the amino acid sequence A (SEQ ID NO:5), the Gln repeat number, in other words, n, is under 150. Furthermore, within its sequence, the $(Gln)_n$ can contain at least one, for example, from 1 to 5 Lys corresponding to the base sequence AAG.

Encompassed by the present invention is the cDNA that encodes the proteins associated with (or characteristic of) MJD. Specifically encompassed is a cDNA that encodes the polypeptides that contain the aforementioned amino acid sequence A (SEQ ID NO:5); a cDNA that possesses the base sequence (hereafter referred to as the base sequence B, SEQ ID NO:4) combined with the CGG part of the base sequence indicated by SEQ ID NO: 7 in which the AAA part of the base sequence indicated by SEQ ID NO: 6 intervenes with $(CXX)_n$, (whereby within the equation, CXX indicates the base sequence CAG, CAA or AAG, and n represents an integer less than 150; however, the numbers of CAA and AAG are from 0 to 5 respectively); a cDNA that possesses the base sequence (hereafter referred to as base sequence C) combined with the CGG part of the base sequence indicated in SEQ ID NO: 9 in which the AAA part of the base sequence indicated by SEQ ID NO: 8 intervenes with $(CXX)_n$ (whereby within the equation, the CXX and n represent the identical significance); and the cDNA and the fragments thereof that have a base sequence of selective hybridization are contained in the base sequence indicated by the aforementioned base sequence B (SEQ ID NO:4) or C (SEQ ID NO:8).

In general, the cDNA indicated by the aforementioned base sequence B (SEQ ID NO:4) or C (SEQ ID NO:8), comprises at least about 300 base pairs, preferably 450 base pairs and even more preferably 600, 750 or 900 base pairs, for example, and the sequence similarity is at least 70%, preferably 80%, more preferably 90%, and most preferably over 95%.

The cDNA, and cDNA fragments indicated in base sequence B (SEQ ID NO:4) or C (SEQ ID NO:8) signify a base portion of at least 10 base pairs, preferably at least 45 bases, for example, 60, 75, 90, 120 or 150 bases.

It has been determined that the CAG repeat in normal, healthy persons ranges from a few times to 30 times, and that in MJD patients it is approximately 60 times. Accordingly, the number of CAG repeats, in other words, the n is less than 150 in the base sequence indicated in base sequence B (SEQ ID NO:4) or C (SEQ ID NO:8). Of the base sequences indicated by base sequence B (SEQ ID NO:4), C SEQ ID NO:8 (and D (SEQ ID NO:11) to be mentioned hereafter), the CXX represents the CAG, CAA or AAG, but in each case, the numbers of CAA and AAG are from 0 to 5.

The gene associated with MJD is a gene with at least 5 exons that was mapped in the human gene 14q24.3-32.1. Applicants have sequenced the entirety of the exons and a part of the introns. The remaining intron sequences can be obtained using the same standard techniques. Specifically, the MJD gene is a chromosomal DNA with a base sequence (to be referred to as base sequence D hereafter) indicated in SEQ ID NO: 11 in which the AGA portion of the base sequence indicated by SEQ ID NO: 10 intervenes with $(CXX)_n$. Revealed in the base sequence D (SEQ ID NO:11) is the base sequence of the intron portion, which is situated above the exon part (to be called number 4 exon in this invention) that includes the CAG repeat.

It was found that the CAG repeat in normal, healthy persons ranges from a few times to 30 times, and that in MJD patients typically is approximately 60–90 times. Accordingly, the n is defined to be less than 150 in the base sequence D (SEQ ID NO:11). It is reasonable to believe that the number of CAG repeats is intricately related to the patient's age at the onset of the disease and the clinical severity of the disease. Thus, the process of determining the number of CAG repeats can also be used as a way to diagnose MJD.

The cDNA and the genes in the present invention can be obtained by gene recombination, chemical synthesis or by other methods known to those in the field.

The cDNA with the base sequence indicated by the base sequence B (SEQ ID NO:4) or C (SEQ ID NO:8), or the gene that encodes a base sequence indicated by base sequence D can be produced according to the following method:

(i) producing a probe with a CAG repeat or a CTG repeat complementary to it;

(ii) screening the human cDNA library by using the probe produced in (i) above;

(iii) screening the human genomic library with the positive clone obtained in (ii) as a probe;

(iv) gene mapping the positive clone that was obtained;

(v) testing the clone that is mapped in 14q24.3-32.1.

The detailed methods at each step were performed according to one of the procedures described herein. Once the base sequence, indicted by the base sequence amino acid sequence B, nucleic acid sequence C (SEQ ID NO:8) or nucleic acid sequence D (SEQ ID NO:11), was determined, the DNA, cDNA or RNA in the present invention could be obtained through chemical synthesis, by PCR methodology, or by hybridization in which a fragment of the base sequence is used as a probe. Furthermore, it was possible to obtain the necessary amount of the objective DNA by introducing an expression vector containing the DNA into an appropriate host cell.

The following are methods that can be used to produce the MJD protein or polypeptides of the present invention (for example, the polypeptide that contains the amino acid sequence A, SEQ ID NO:5). For example, the protein can be isolated from the host organism or from cultured cells using standard laboratory techniques, by chemical synthesis and by recombinatory technique, known to those of skill in the art. The protein can be expressed in a number of appropriate hosts, including, for example, bacteria, yeast, insect cells and mammalian cells.

For example, a DNA construct useful to produce the MJD protein in E. coli, can be made comprising the DNA that encodes the MJD protein, or a biologically active fragment thereof, (for example, the DNA that encodes the base sequence indicated by the base sequence B) and an appropriate promoter (for example, the trp promoter, the lac promoter, the hPL promoter, or the T7 promoter). The expression vector is produced by inserting the DNA construct into an appropriate vector that permits expression within the E. coli (for example, the pBR322, the pUC18, or the pUC19). Next, the E. coli that was transformed by this expression vector (for example, the E. coli DH1, the E. coli JM109, or the E. coli HB1O1 strain can be cultivated in the appropriate culture, and the expressed proteins can be recovered from culture. Moreover, if a bacterial signal peptide (for example, the pe1B signal peptide) is used, it is possible to express the proteins into the periplasm. Furthermore, it is possible to produce a fusion protein wherein the MJD protein is fused with the other polypeptides e.g., useful for detection of the expressed protein.

When mammalian cells are used for the expression, for example, the expression vector is produced by inserting the DNA that encodes the base sequence indicated by the base sequence C with the appropriate promoter (for example, the SV40 promoter, the LTR promoter, or the metallothionein promoter) within the appropriate vector (for example, a retrovirus vector, a papilloma virus vector, a vaccinia virus vector, or the SV40 strain vector). Next, the appropriate mammalian cells (for example, C0S-7 cells, CH0 cells or L cells) are transformed with the expression vector, and the proteins were expressed into the culture solution during the cultivation of the transformation organism in an appropriate culture. The expressed proteins can be isolated and purified by standard biochemical methods.

The present invention encompasses expression vectors that contain the cDNA or gene of the present invention. The vectors of the present invention can also include selective marker genes, such as the ampicillin gene.

Also encompassed in the present invention are host cells transformed by the expression vectors described herein. Examples of host cells include bacteria, yeast, insect cells and mammalian cells.

The protein associated with MJD described herein can be used in treating MJD. For example, the expression vector that contains the DNA construct that encodes the MJD protein in the present invention (whereby the CAG repeat is within the normal range) is administered generally or locally (ideally, it is administered locally through the generally accepted targeting method). The vector enters into the brain cells, integrates with the gene and intermittently expresses the protein associated with MJD possessing the CAG repeat within the normal range. When the normal MJD protein is expressed in tremendous excess of the abnormal MJD protein the abnormal protein loses its dominance.

In the present invention, the protein associated with MJD or fragments thereof can be used to raise antibodies reactive with the MJD protein. These antibodies (either polyclonal antibodies or monoclonal antibodies) can be used to determine the presence of abnormal Machado-Joseph Disease protein and/or quantify the amount of MJD protein that is present in the individual. As a result, the protein can be used to study the relationship between this protein (gene) and the disease, or to diagnose the disease. At the present time, the protein and gene used in the present invention are only studied in relation to the MJD, but we cannot rule out the possibility of its association with diseases other than the MJD, such as those of the degeneration of the cerebellum or an entirely different disease. There is even the possibility that it is a protein that has a completely new biological activity. Thus, the MJD protein is significant and carries great potential. Polyclonal antibodies and the monoclonal antibodies can be produced using techniques well known to those of skill in the art.

The cDNA in the present invention serves not only as the essential and necessary template for the production of the protein for this invention, but also as an effective treatment for MJD. In for example, by the administration of a expression vector containing anti-sense DNA, it is possible to completely inhibit or decrease the expression of abnormal MJD protein. Moreover, it is possible to use the cDNA in the present invention as the probe in the isolation of the genomic DNA.

Furthermore, it is also possible to isolate the gene that is considered to be responsible for the degeneration of the cerebellum other than the MJD, believed to possess a genetic sequence that is highly homologous to the gene associated with the MJD.

The gene in the present invention can be utilized in the diagnosis of MJD. It is believed that the quantity of the CAG repeat is intricately related to the patient's age at the onset of the disease and the clinical severity of the disease. Accordingly, by determining the number of CAG trinucleotide repeats, it is possible to predict the onset of the disease (e.g., determining the risk of being affected by MJD) and, to predict the severity of symptoms after its onset.

In order to determine the number of the CAG triplet repeats, the PCR method can be used, in which sequence on both sides of the CAG repeat portion comprise the primers. For example, a random 10 to 30 nucleotides of the intron portion (indicated by the SEQ ID NO: 12) that is located on the 5' end of the CAG repeat, and a random 10 to 30 nucleotides of the portion (indicated by the SEQ ID NO: 13) situated on the 3' end of the CAG repeat can be used as primers, and the genes or mRNA of the test sample obtained from the individual can be amplified. The amplified products can be evaluated by e.g., agarose electrophoresis. Preferred primes are as follows: SEQ ID NO: 14 (5'–CCAGTGACTACTTTGATT CG–3'); SEQ ID NO: 15 (5—TGGCCTTTCACATGGATGTGAA—3'); and SEQ ID NO: 16 (5'—CTTACCTAGATCACTCCCAA—3'). These preferred primers can be paired in the PCR method as follows: SEQ ID NO: 14 and SEQ ID NO: 15 or SEQ ID NO: 14 and SEQ ID NO: 16. The PCR conditions can be established by standard laboratory methods. For example, the conditions can be as follows: sample DNA (gene) 200 ng and each primer at 200 ng; 50 mM KCl; 10 mM Tris buffer solution (pH 8.8); 1.5 mM MgCl 2; 0.1% Triton×100; 10% (v/v) DMSO; 5 unit Taq polymerase (manufactured by Wako Chemicals, Inc.) with a total amount of 20 $\mu$l;95° C.; 5 minutes—>(95° C.; 1 minute—>57° C.; 1 minute—>72° C.; 1 minute)×25 cycle—>72° C.; 10 minutes. The DNA samples used here were taken from the DNA or RNA processed from the tissues (from the blood, for example) of a healthy person or those of a patient afflicted by MJD. The CAG repeat number determined the length of the PCR product as assayed by electrophoresis. Preferably, sequencing can be performed after subcloning the PCR product into vector DNA (e.g., Bluescript LK(-).

The following examples more specifically illustrate the invention and are not intended to be limiting in any way.

Example 1

Cloning the MJD Gene

A probe with a sequence that had 12 CTG trinucleotide repeats (which was homologous to the CAG repeat) (SEQ ID NO: 17) 5' GATCT (CTG)$_{12}$ G 3' was synthesized, and a screening was conducted on the cDNA library (J. Biol. Chem., 268:3728 (1993)) processed through the mRNA from the human cerebral temporal cortex.

The endo-labeling method utilizing polynucleotide kinase (PNK 103™, manufactured by Toyo Textiles, Inc.) was used to label the probe. 50,000 plaques obtained from the library were screened and 30 positive clones were obtained. Hybridization was performed using 1 M NaCl; 500 mM Tris base buffer solution (pH 7.5); 1% SDS; 200 $\mu$g/ml yeast RNA at 55° C. for 16 hours, and autoradiography was performed after they were cleansed 4 times with 2×SSC, 0.1% SDS, at 55° C. for 30 minutes.

When the clones were cut by means of the restriction enzyme Rsa1 and analyzed by utilizing the southern blotting method, a positive band was clearly confirmed in 21 clones. Of these, 8 clones with the highest density (i.e., those having the highest degree of hybridization) were selected and subcloned using the EcoRI site of the pBluescript SK(+) (manufactured by Stratagene Company). A cDNA clone (CAG-27) was obtained, which contained a CAG repeat region. The entirety of CAG-27 contained 1807 bp, with an open reading frame composed of 359 amino acids. A homology was discovered with the Genbank, HUMSW×784 human×chromosome STS, as a result of the homology examination.

Example 2

Determining the Expansion of the CAG Repeat

RNA was extracted from the brain, spinal cord, heart, lungs, stomach, liver, small intestines, large intestines, pancreas, spleen, kidneys, muscles and the seminal glands of the SD type male rats (14 weeks in age), and for each one, the poly A RNA was purified. In each case, the 10 $\mu$g of poly A RNA was isolated, according to the standard method using the agarose electrophoresis. The RNA was transferred to a nylon membrane (Hybond plus™; manufactured by Amersham Company) and analyzed using the northern blotting method by using a fragment of the BamHI/Gg1II fragment of the CAG-27 as a probe. All organs except for the pancreas and the seminal glands, a positive band was discovered at a macromolecular level from 28S. (In the case of the seminal glands, the band was around 18S.)

In an attempt to determine the size of the CAG repeat by means of PCR, 2 sets of primers (one in which the primers (SEQ ID NO: 18) and (SEQ ID NO: 19) mentioned below were combined and another in which the same (SEQ ID NO: 20) and (SEQ ID NO: 21) were combined) were made that on either side this portion.

877—TCTTACTTCAGAAGAGCTTCGGAAG—901 (SEQ ID NO: 18)

1047—GCTGGCCTTTCACATGGATGTGAAC—1023 (SEQ ID NO: 19)

904—ACGAGAAGCCTACTTTGA—921 (SEQ ID NO: 20)

1025—AACTCTGTCCTGATAGGT—1008 (SEQ ID NO: 21)

DNA obtained from leukocytes of a healthy person was used in the combination of these 2 sets of primers and was tested under various conditions. Amplification due to the PCR was impossible to detect, suggesting the possibility of the presence of intron within the structure of the CAG repeat or in its environ.

By means of a sequential analysis, it was discovered, for example, that the MJD gene was mapped in the human chromosome 14q24.3-32.1. In order to determine whether or not the clone that was obtained, CAG-27, was associated with MJD, chromosome mapping was performed by using the fluorescence in situ hybridization (Fish) method. However, a clear result could not be obtained due to the large number of non-specific images. Given these results, the next step was to perform gene cloning on these clones.

A fragment of the BamHI/BglII fragment of the CAG-27 clone was used as a probe to screen 500,000 clones from the human genomic library. (The screening was conducted under the same conditions as those for the hybridization in Example 1, with the exception of the absence of the 65° C.

temperature.) As a result, 12 positive clones were obtained. Each of these clones were cut by means of XhOI/PstI, and analyzed using the southern blotting method. Two clones giving the strongest signals (named CAG-27-6 and CAG-27-11 respectively) were subjected to chromosome mapping using the Fish method.

As a result, it was determined that both CAG-27-6 and CAG-27-11 were mapped to the 14q24.3-32.1 chromosome, the genetic locus for MJD. The two clones were cut by PstI and subcloned on the pBluescript SK(+), and the positive clones in the hybridization were sequenced.

It was found that, in each case, the positive clones contained a part corresponding to 287 to 372 of the CAG-27. Further testing was conducted on an additional 790,000 plaques in the human brain cDNA library by using the BamHI-BglII fragment of the CAG-27 as a probe. As a result, 2 different types of cDNA (cDNA-3 and cDNA-6) other than the CAG-27 were obtained.

As a result of the sequencing, in the cDNA-6, there was a correspondence with the base of the CAG-27, the part from 1–287 and from 373–924. In the cDNA-3, there was a correspondence with the base of the CAG-27, the part from 1–287. Accordingly, these three can be considered to be three mRNA isoforms that were respectively produced from the splicings of the identical genes. In particular, the splicing of the base 924 position was immediately before the CAG repeat, and it was clearly shown that a side of the 3' intron must be used with the PCR.

The DraII/SacI fragment (corresponding to the end of the carboxyl of the protein coded in the final portion of the CAG repeat) of the CAG-27 was used as a probe to screen the human genomic library. Four positive clones were 30 obtained from 800,000. (They were respectively named CAG-27-21, CAG-27-22, CAG-27-23 and CAG-27-24. The screening was conducted under the same conditions as those for the hybridization in Example 1, with the exception of the absence of the 65° C. temperature.) Of these, the CAG-27-23 was sequenced, and as a result, the intron structure of the base of the 924 position (the base immediately before the CAG repeat) of the CAG-27 was determined. (See SEQ ID NO: 12.)

Here, it was revealed that the CAG repeats obtained in the genomic clone was 27 times and, therefore, different from the 26 times obtained by the cDNA (CAG-27).

New PCR primers were created: 5'—CCAGTGACTACTTTGATFCG—3', (the 5' side of the CAG repeat existing within the intron portion SEQ ID NO: 14); 5'—TGGCCTTTCACATGGATGTGAA–3', (the 3' side of the CAG repeat, SEQ ID NO: 15); and 5'—CTTACCTAGATCACTCCCAA—3', (the 3' side of the CAG repeat, SEQ ID NO: 16).

When the primer (SEQ ID NO: 14) and the primer (SEQ ID NO: 15) were combined, there was a specimen distinct from that which underwent PCR. There was complete success when primers (SEQ ID NO: 14) and (SEQ ID NO: 16) were combined. PCR was performed in the following way: sample DNA (gene) 200 ng; primer (SEQ ID NO: 14) and primer (SEQ ID NO: 16) respectively at 200 ng; 50 mM KC1; 10 mM Tris buffer solution (pH 8.8); 1.5 mM $MgCl_2$; 0.1% Triton×100; 10% (v/v) DMSO; 5 units Taq polymerase (manufactured by Wako Chemicals, Inc.) with a total amount of 20 μg 1. (The PCR was performed under the following conditions: 95° C.; 5 minutes—>[95° C.; 1 minute—>57° C.; 1 minute—>72° C; 1 minute]×25 cycle—>72° C.; 10 minutes.) After the reaction, agarose electrophoresis was performed according to standard procedures. As a result, it was determined that whereas normal, healthy persons had a band that corresponded to a CAG repeat of 13 to 36 times, all the patients with MJD (11 cases) had a CAG repeat of approximately 60 times (from 61 to 90 times). Accordingly, it was established that these conditions could be used in the genetic diagnosis of the MJD.

Example 3

Distribution of CAG repeats of the MJD1 gene in normal population

MATERIALS AND METHODS

Amplification of the CAG repeats

All patient and normal control DNA were obtained by extraction from leukocytes. MJ-N (5'–TCGTGAAACAATGTATTTTCCTTATG–3') (SEQ ID NO: 22) MJ-RN (5'–GATGTGAACTCTGTCCTGAT–3') (SEQ ID NO: 23) were used as primer pairs for PCR analysis. Amplification was carried out for 30 cycles (1 min denaturation at 95° C., 1 min annealing at 55° C., 1 min elongation at 72° C.). Two hundred ng genomic DNA was used for PCR reaction in 20 μl of 10mM Tris-HCl (pH 8.3), 50 MM KC1, 1.5 MM $MgCl_2$, 0.1% Triton X-100, 10% DMSO, 250 μM dCTP, dATP, TTP, 62.5 μM dGTP, 187.5 μM 7-deaza dGTP, 200 ng MJ-RN primer (SEQ ID NO:23), 180 ng MJ-N primer (SEQ ID NO:22), 20 ng 5'-$^{32}$P MJ-N primer (SEQ ID NO:22) and 5 U of AmpliTaq polymerase (Perkin Elmer). Gel electrophoresis was performed on 8% HydroLink Long Ranger (AT Biochem, Pa., USA) gel with 42% formamide. Without formamide, the PCR products with long CAG repeats are one to three repeats shorter than the sequence determined repeat length.

For parent-child analysis and sib-sib analysis, family members were analyzed side by side on the same gel and produced at least twice.

Clinical and statistical analyses

The diagnosis and the classification of subtypes were performed according to 'Clinical criteria for diagnosis of Machado-Joseph disease' (Lima, L. and Coutinho, P., Neurology, 30:319–322 (1980)), and with the help of MRI, CT and electrophysiological studies. 'The age of onset' is defined as the age when the patient first noticed any symptoms.

The statistical analyses were performed with JMP software (SAS Institute, Inc.).

Two hundred and two chromosomes in normal individuals (101) displayed a range from 14 to 34 repeat units. The mean was 21.8 repeats and the median was 24 repeats. Heterozygosity was 91%. Fourteen repeat units were the most common (34%) and the shortest, and the second peak was at 27–28 repeat units.

Repeat length on MJD chromosomes

First the CAG repeat length of the patients from pathologically definite MJD families was determined. All 20 patients examined from these six new families showed the CAG expansions in the MJD1 gene. Fifty-four patients from 43 families (among 61 clinically diagnosed or suspected MJD patients from 50 families) showed expansions. The remaining seven patients did not show expansions, although they had partial, but not complete MJD phenotypes. Six unclassified spinocerebellar degeneration patients from six families also showed the expansion. Altogether the CAG repeat expansions are now confirmed in the MJD1 gene among 80 new patients from 55 families. Further analyses were performed on all (90) of the above 80 chromosomes together with the previously identified 10 chromosomes except for one MJD1 chromosome, which had been determined from an autopsied brain (10). These MJD1 chromosomes contained 61–84 repeat units. The median was 75 repeats and the distribution was normal (mean=74.7, standard deviation=4.1). MJD chromosomes were completely discrete from normal chromosomes.

Age of onset and CAG repeat length

The relationship between the age of onset and the CAG repeat length in the expanded allele in affected individuals was investigated. A highly significant inverse correlation (n=83, r=−0.87, p<$10^{-4}$) was noted for the length of CAG repeat and the age of onset of the disease. The repeat length accounted for approximately 80% of total variation in the age of onset ($r^2$=0.76).

Intergenerational variation in the age of onset and repeat length

Possible clinical anticipation in the age of onset of both affected parent and child (nine pairs) was also examined. The mean age of onset of the parent is 43.6±2.6 years old, and in the child 29.4±2.6 years old (mean±standard error). The difference in the age of onset between affected parent and difference in the age of onset between affected parent and affected child is 14.1 years, and is statistically significant (p≦0.0013).

To evaluate the instability of the MJD1 CAG repeat through generations, the length of CAG repeats in affected parent and child pairs was assessed. In the 14 MJD families examined, there were nine paternal-offspring and nine maternal-offspring pairs. The correlation between repeat length in affected parents and children was highly significant (n=18, r=0.88, p<$10^{-4}$). Neither maternal nor paternal transmission showed a decrease in the length of CAG repeats. Seven of the nine maternal transmissions resulted in increases in the length of CAG repeats by an average of 1.4 ranging from 0 to 3. All (nine) of the paternal transmissions resulted in increases by an average of 3.1 ranging from 1 to 6. The difference in the degree of the increase between maternal and paternal transmissions is statistically significant (p±0.038). The results indicate a relatively small increase in CAG repeats and the lack of decrease in the repeats in the MJD1 gene transmission.

Sib-sib correlations of CAG expansions

A total of 19 pairs of siblings were included in this analysis. The length of repeats carried between siblings correlate well (n=19, r=0.80, p<$10^{-4}$). The correlation still holds when the siblings were divided into maternally transmitted (n=12, r=0.96, p<$10^{-4}$) and paternally transmitted groups (n =7, r=0.87, p<0.012). Nine of the 12 maternal transmissions had an average difference of 1.4 repeats between siblings (range 0–4). Six of the seven paternal transmissions had an average difference of 3.6 repeats between siblings (range 0–9). This difference between maternal and paternal transmissions is significant (p=0.064). The length of CAG repeats of sib 1 was inversely correlated to the difference in repeat length when transmitted paternally (n=7, r=−0.95, p≦0.001).

Relation of the subtype and the reseat length

MJD is divided into three clinical subtypes. The subtype partially correlates with the age of onset (type I, type II and type III). The relation of the subtypes to the age of onset and to the repeat length was also studied. The age of onset of type I (n=9), type II (n=64), and type III (n=9), type II 1.5, and 39.8±3.8 years old (mean±standard error), respectively. These differences are statistically significant between type I and type II, and between type I and type III (p<0.05; Tukey-Kramer HSD). The length of expanded CAG repeats of type I, type II, and type III were 79.4±1.0, 74.6±0.5, and 72.6±1.1 (mean, standard error), respectively. The difference is statistically significant between type I and type II, and between type I and type III (p<0.05; Tukey-Kramer HSD). The number of patients of maternal and paternal transmissions were five and four in type I, 26 and 29 in II, and five and three in III, respectively. Type I showed larger expanded CAG repeats and younger onset, but was not related to the paternal transmission.

Equivalents

Those skilled in the art will recognize, or be able to ascertain using no more than routine experimentation, many equivalents to specific embodiments of the invention described specifically herein. Such equivalents are intended to be encompassed in the scope of the following claims.

---

We claim:

1. A method of determining whether an expanded nucleotide CAG triplet repeat, or its fully complementary sequence, is present in DNA in an individual, said expanded triplet being characteristic of Machado-Joseph Disease, comprising the steps of:
  a) obtaining DNA from an individual; and
  b) determining the presence of an expanded CAG triplet repeat, or its fully complementary sequence, in the DNA,
  wherein the presence of an expanded CAG triplet repeat in the DNA is indicative of the presence of Machado-Joseph Disease in the individual.

2. A method of predicting whether an individual is likely to be affected with Machado-Joseph Disease, comprising the steps of:
  a) obtaining DNA from the individual; and
  b) determining the presence of an expanded CAG triplet repeat, or its fully complementary sequence, in the DNA obtained in a),
wherein if an expanded CAG triplet repeat is present, the individual is likely to be affected with Machado-Joseph Disease.

3. The method of claim 2 wherein the DNA is obtained from human chromosome 14q32.1.

4. The method of claim 2 wherein the expanded CAG triplet repeat of an individual likely to be affected with Machado-Joseph Disease is greater than or equal to 60 repeats.

5. The method of claim 2 wherein the expanded CAG triplet repeat of an individual not likely to be affected with Machado-Joseph Disease is less than or equal to 40 repeats.

6. The method of claim 1, which includes amplifying DNA containing said repeated CAG triplet sequence, or its fully complementary sequence, using a nucleic acid sequence amplification process.

7. The method of claim 1 wherein the method comprises hybridizing a sample of genomic DNA or cDNA from an individual with a hybridization probe which hybridizes with all or a portion of SEQ ID NO:1 or its fully complementary sequence.

8. The method of claim 7 wherein the hybridization probe comprises all or a portion of SEQ ID NO:1 or its fully complementary sequence.

9. A method of determining whether an expanded nucleotide CAG triplet repeat, is present in the RNA of an individual, said expanded triplet being characteristic of Machado-Joseph Disease, comprising the steps of:
  a) obtaining RNA from an individual; and
  b) determining the presence of an expanded CAG triplet repeat, in the RNA,
  wherein the presence of an CAG triplet repeat in the RNA is indicative of the presence of Machado-Joseph Disease in the individual.

10. A method of predicting whether an individual is likely to be affected with Machado-Joseph Disease, comprising the steps of:

a) obtaining RNA from the individual; and b) determining the presence of an expanded CAG triplet repeat, in the RNA obtained in a), wherein if an expanded CAG triplet repeat is present, the individual is likely to be affected with Machado-Joseph Disease.

11. The method of claim 10 wherein the RNA hybridizes to human chromosome 14q32.1.

12. The method of claim 10 wherein the expanded CAG triplet repeat of an individual likely to be affected with Machado-Joseph Disease is greater than or equal to 60 repeats.

13. The method of claim 10 wherein the expanded CAG triplet repeat of an individual not likely to be affected with Machado-Joseph Disease is less than or equal to 40 repeats.

14. The method of claim 9 which includes amplifying RNA containing said repeated CAG triplet sequence, using a nucleic acid sequence amplification process.

15. The method of claim 9 wherein the method comprises hybridizing a sample of RNA from an individual with a hybridization probe which hybridizes with all or a portion of SEQ ID NO:1.

16. The method of claim 9 wherein the hybridization probe comprises all or a portion of SEQ ID NO:1 or its complement.

17. A method of determining whether an expanded CAG triplet repeat, or its fully complementary sequence, is present in DNA from an individual, said expanded triplet repeat being characteristic of Machado-Joseph Disease, comprising the steps of:

a) obtaining DNA from an individual; and b) determining the presence of an expanded CAG triplet repeat, or its complement, in the DNA by polymerase chain reaction techniques, wherein the presence of an expanded CAG triplet repeat in the DNA is indicative of the presence of Machado-Joseph Disease in the individual.

18. The method of claim 17 wherein the polymerase chain reaction technique uses two primer nucleotide sequences, wherein the first primer sequence comprises a nucleotide sequence located on the 5' side of the CAG repeat region of the Machado-Joseph Disease gene and the second primer sequence comprises a nucleotide seqeunce located on the 3' side of CAG repeat region.

19. The method of claim 18 wherein the polymerase chain reaction technique uses two primer sequences, wherein the first primer sequence comprises about 10 to about 30 base pairs located on the 5' side of the CAG repeat region of the Machado-Joseph Disease gene and the second primer sequence comprises about 10 to about 30 base pairs located on the 3' side of the CAG repeat region.

20. The method of claim 19 wherein the primer sequences are selected from the group consisting of SEQ ID NO: 14, SEQ ID NO: 15, SEQ ID NO: 16, SEQ ID NO: 17, SEQ ID NO: 22 and SEQ ID NO: 23.

21. A kit for diagnosing Machado-Joseph Disease in an individual, wherein Machado-Joseph Disease is characterized by the presence of an expanded CAG triplet repeat region, and diagnosis comprises hybridizing a sample of DNA or RNA from an individual with a nucleic acid probe, wherein the kit contains a nucleic acid probe comprising a nucleic acid complementary to the CAG triplet repeat region and to flanking the CAG repeat regions of SEQ ID NO:1 or its fully complementary sequence, whereby the presence of an expanded CAG triplet is determined.

22. A method of predicting whether an individual is likely to be affected with Machado-Joseph Disease comprising the steps of:

a) obtaining DNA from an individual; and b) determining the presence of an expanded CAG repeat, or its fully complementary sequence, in the DNA obtained in a), by polymerase chain reaction techniques, wherein if an expanded CAG triplet repeat is present, the individual is likely to be affected with Machado-Joseph Disease.

23. The method of claim 22 wherein the DNA is obtained from human chromosome 14q32.1.

24. The method of claim 22 wherein the polymerase chain reaction technique uses two primer nucleotide sequences, wherein the first primer sequence comprises a nucleotide sequence located on the 5' side of the CAG repeat region of the Machado-Joseph Disease gene and the second primer sequence comprises a nucleotide seqeunce located on the 3' side of CAG repeat region.

25. The method of claim 24 wherein the polymerase chain reaction technique uses two primer sequences, wherein the first primer sequence comprises about 10 to about 30 base pairs located on the 5' side of the CAG repeat region of the Machado-Joseph Disease gene and the second primer sequence comprises about 10 to about 30 base pairs located on the 3' side of the CAG repeat region.

26. The method of claim 25 wherein the primer sequences are selected from the group consisting of SEQ ID NO:14, SEQ ID NO:15, SEQ ID NO:16, SEQ ID NO:17, SEQ ID NO:22 and SEQ ID NO:23.

27. The method of claim 22 wherein the expanded CAG triplet repeat of an individual likely to be affected with Machado-Joseph Disease is greater than or equal to 60 repeats.

28. The method of claim 22 wherein the expanded CAG triplet repeat of an individual not likely to be affected with Machado-Joseph Disease is less than or equal to 40 repeats.

29. A kit for diagnosing Machado-Joseph Disease in an individual, wherein Machado-Joseph Disease is characterized by the presence of an expanded CAG triplet repeat region, and diagnosis comprises determining the presence of an expanded CAG triplet repeat region in the Machado-Joseph Disease gene by polymerase chain reaction techniques, wherein the polymerase chain reaction technique uses two primer nucleotide sequences, wherein the first primer sequence comprises about 10 to about 30 base pairs located on the 5' side of the CAG repeat region of the Machado-Joseph Disease gene and the second primer sequence comprises about 10 to about 30 base pairs located on the 3' side of the CAG repeat region.

30. The method of claim wherein the primers are selected from the group consisting of: SEQ ID NO.14; SEQ ID NO:15; SEQ ID NO:16; SEQ ID NO:17; SEQ ID NO:22 and SEQ ID NO:23.

* * * * *

UNITED STATES PATENT AND TRADEMARK OFFICE
CERTIFICATE OF CORRECTION

PATENT NO. : 5,840,491
DATED : November 24, 1998
INVENTOR(S) : Akira Kakizuka

It is certified that error appears in the above-identified patent and that said Letters Patent is hereby corrected as shown below:

In Claim 21, column 36, line 3, after "and to" insert ---sequence---.

In Claim 30, column 36, line 56 after "method of claim" insert ---29---.

Signed and Sealed this

Eighteenth Day of May, 1999

Attest:

Q. TODD DICKINSON

Attesting Officer    Acting Commissioner of Patents and Trademarks

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 1776 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 36..1115

( x i ) SEQUENCE DESCRIPTION: SEQ ID NO:1:

```
TCGGCGTGGG  GGCCGTTGGC  TCCAGACAAA  TAAAC  ATG  GAG  TCC  ATC  TTC  CAC              53
                                           Met  Glu  Ser  Ile  Phe  His
                                            1                    5

GAG  AAA  CAA  GAA  GGC  TCA  CTT  TGT  GCT  CAA  CAT  TGC  CTG  AAT  AAC  TTA       101
Glu  Lys  Gln  Glu  Gly  Ser  Leu  Cys  Ala  Gln  His  Cys  Leu  Asn  Asn  Leu
               10                   15                   20
```

| | | | | | | | | | | | | | | | | |
|---|---|---|---|---|---|---|---|---|---|---|---|---|---|---|---|---|
| TTG | CAA | GGA | GAA | TAT | TTT | AGC | CCT | GTG | GAA | TTA | TCC | TCA | ATT | GCA | CAT | 149 |
| Leu | Gln | Gly | Glu | Tyr | Phe | Ser | Pro | Val | Glu | Leu | Ser | Ser | Ile | Ala | His | |
| | | 25 | | | | 30 | | | | | 35 | | | | | |
| CAG | CTG | GAT | GAG | GAG | GAG | AGG | ATG | AGA | ATG | GCA | GAA | GGA | GGA | GTT | ACT | 197 |
| Gln | Leu | Asp | Glu | Glu | Glu | Arg | Met | Arg | Met | Ala | Glu | Gly | Gly | Val | Thr | |
| | 40 | | | | | 45 | | | | 50 | | | | | | |
| AGT | GAA | GAT | TAT | CGC | ACG | TTT | TTA | CAG | CAG | CCT | TCT | GGA | AAT | ATG | GAT | 245 |
| Ser | Glu | Asp | Tyr | Arg | Thr | Phe | Leu | Gln | Gln | Pro | Ser | Gly | Asn | Met | Asp | |
| 55 | | | | 60 | | | | 65 | | | | | | | 70 | |
| GAC | AGT | GGT | TTT | TTC | TCT | ATT | CAG | GTT | ATA | AGC | AAT | GCC | TTG | AAA | GTT | 293 |
| Asp | Ser | Gly | Phe | Phe | Ser | Ile | Gln | Val | Ile | Ser | Asn | Ala | Leu | Lys | Val | |
| | | | | 75 | | | | | 80 | | | | | 85 | | |
| TGG | GGT | TTA | GAA | CTA | ATC | CTG | TTC | AAC | AGT | CCA | GAG | TAT | CAG | AGG | CTC | 341 |
| Trp | Gly | Leu | Glu | Leu | Ile | Leu | Phe | Asn | Ser | Pro | Glu | Tyr | Gln | Arg | Leu | |
| | | | 90 | | | | | 95 | | | | | 100 | | | |
| AGG | ATC | GAT | CCT | ATA | AAT | GAA | AGA | TCA | TTT | ATA | TGC | AAT | TAT | AAG | GAA | 389 |
| Arg | Ile | Asp | Pro | Ile | Asn | Glu | Arg | Ser | Phe | Ile | Cys | Asn | Tyr | Lys | Glu | |
| | | | 105 | | | | 110 | | | | 115 | | | | | |
| CAC | TGG | TTT | ACA | GTT | AGA | AAA | TTA | GGA | AAA | CAG | TGG | TTT | AAC | TTG | AAT | 437 |
| His | Trp | Phe | Thr | Val | Arg | Lys | Leu | Gly | Lys | Gln | Trp | Phe | Asn | Leu | Asn | |
| | 120 | | | | | 125 | | | | | 130 | | | | | |
| TCT | CTC | TTG | ACG | GGT | CCA | GAA | TTA | ATA | TCA | GAT | ACA | TAT | CTT | GCA | CTT | 485 |
| Ser | Leu | Leu | Thr | Gly | Pro | Glu | Leu | Ile | Ser | Asp | Thr | Tyr | Leu | Ala | Leu | |
| 135 | | | | | 140 | | | | | 145 | | | | | 150 | |
| TTC | TTG | GCT | CAA | TTA | CAA | CAG | GAA | GGT | TAT | TCT | ATA | TTT | GTT | GTT | AAG | 533 |
| Phe | Leu | Ala | Gln | Leu | Gln | Gln | Glu | Gly | Tyr | Ser | Ile | Phe | Val | Val | Lys | |
| | | | | 155 | | | | | 160 | | | | | 165 | | |
| GGT | GAT | CTG | CCA | GAT | TGC | GAA | GCT | GAC | CAA | CTC | CTG | CAG | ATG | ATT | AGG | 581 |
| Gly | Asp | Leu | Pro | Asp | Cys | Glu | Ala | Asp | Gln | Leu | Leu | Gln | Met | Ile | Arg | |
| | | | 170 | | | | | 175 | | | | | 180 | | | |
| GTC | CAA | CAG | ATG | CAT | CGA | CCA | AAA | CTT | ATT | GGA | GAA | GAA | TTA | GCA | CAA | 629 |
| Val | Gln | Gln | Met | His | Arg | Pro | Lys | Leu | Ile | Gly | Glu | Glu | Leu | Ala | Gln | |
| | | 185 | | | | | 190 | | | | | 195 | | | | |
| CTA | AAA | GAG | CAA | AGA | GTC | CAT | AAA | ACA | GAC | CTG | GAA | CGA | ATG | TTA | GAA | 677 |
| Leu | Lys | Glu | Gln | Arg | Val | His | Lys | Thr | Asp | Leu | Glu | Arg | Met | Leu | Glu | |
| | 200 | | | | | 205 | | | | | 210 | | | | | |
| GCA | AAT | GAT | GGC | TCA | GGA | ATG | TTA | GAC | GAA | GAT | GAG | GAG | GAT | TTG | CAG | 725 |
| Ala | Asn | Asp | Gly | Ser | Gly | Met | Leu | Asp | Glu | Asp | Glu | Glu | Asp | Leu | Gln | |
| 215 | | | | | 220 | | | | | 225 | | | | | 230 | |
| AGG | GCT | CTG | GCA | CTA | AGT | CGC | CAA | GAA | ATT | GAC | ATG | GAA | GAT | GAG | GAA | 773 |
| Arg | Ala | Leu | Ala | Leu | Ser | Arg | Gln | Glu | Ile | Asp | Met | Glu | Asp | Glu | Glu | |
| | | | | 235 | | | | | 240 | | | | | 245 | | |
| GCA | GAT | CTC | CGC | AGG | GCT | ATT | CAG | CTA | AGT | ATG | CAA | GGT | AGT | TCC | AGA | 821 |
| Ala | Asp | Leu | Arg | Arg | Ala | Ile | Gln | Leu | Ser | Met | Gln | Gly | Ser | Ser | Arg | |
| | | | 250 | | | | | 255 | | | | | 260 | | | |
| AAC | ATA | TCT | CAA | GAT | ATG | ACA | CAG | ACA | TCA | GGT | ACA | AAT | CTT | ACT | TCA | 869 |
| Asn | Ile | Ser | Gln | Asp | Met | Thr | Gln | Thr | Ser | Gly | Thr | Asn | Leu | Thr | Ser | |
| | | 265 | | | | | 270 | | | | | 275 | | | | |
| GAA | GAG | CTT | CGG | AAG | AGA | CGA | GAA | GCC | TAC | TTT | GAA | AAA | CAG | CAG | CAA | 917 |
| Glu | Glu | Leu | Arg | Lys | Arg | Arg | Glu | Ala | Tyr | Phe | Glu | Lys | Gln | Gln | Gln | |
| | 280 | | | | | 285 | | | | | 290 | | | | | |
| AAG | CAG | CAA | CAG | CAG | CAG | CAG | CAG | CAG | CAG | CAG | CAG | CAG | CAG | CAG | CAG | 965 |
| Lys | Gln | Gln | Gln | Gln | Gln | Gln | Gln | Gln | Gln | Gln | Gln | Gln | Gln | Gln | Gln | |
| 295 | | | | | 300 | | | | | 305 | | | | | 310 | |
| CAG | CAG | CAG | CAG | CAG | CAG | CAG | CGG | GAC | CTA | TCA | GGA | CAG | AGT | TCA | CAT | 1013 |
| Gln | Gln | Gln | Gln | Gln | Gln | Gln | Arg | Asp | Leu | Ser | Gly | Gln | Ser | Ser | His | |
| | | | | 315 | | | | | 320 | | | | | 325 | | |
| CCA | TGT | GAA | AGG | CCA | GCC | ACC | AGT | TCA | GGA | GCA | CTT | GGG | AGT | GAT | CTA | 1061 |
| Pro | Cys | Glu | Arg | Pro | Ala | Thr | Ser | Ser | Gly | Ala | Leu | Gly | Ser | Asp | Leu | |
| | | 330 | | | | | 335 | | | | | 340 | | | | |

```
GGT AAG GCC TGC TCA CCA TTC ATC ATG TTC GCT ACC TTC ACA CTT TAT      1109
Gly Lys Ala Cys Ser Pro Phe Ile Met Phe Ala Thr Phe Thr Leu Tyr
        345             350                 355

CTG ACA TAAGAGCTCC ATGTGATTTT TGCTTTACAT TATTCTTCAT TCCTCTTTA        1165
Leu Thr
    360

ATCATATTAA GACTCTTAAG TAAATTTGTA ATCTACTAAA TTTCCCTGGA TTAAGGAGCA    1225
AGGTTACCAA AAAAAAAAA AAAAAAAAA GCTAGATGTG GTGGCTCACA TCTGTAATCC      1285
CAGCACTTTG GGAAACCAAG GCAGGAGAGG ATTGCTAGAA CATTTAATGA ATACTTTAAC    1345
ATAATAATTT AAACTTCACA GTAATTTGTA CAGTCTCCAG AAATTCCTTA GACATCATGA    1405
ATATTTTTCT TTTTTTGGGG TGACAGGGCA AAACTCTGTC TCAAAAAAAA AAAAAAAAA     1465
AAAAGGGCTG GACACGGTGG CTTACGCCTG TTATCCCGGC ACTTTGGGAG GCCAAGGCCG    1525
ATGGATCACC TGAGGTCAGG AGTTCAAGAC CAGCCTGGCC AACATGGTGA AACCCCATCT    1585
CTACTAAAAA TACAAAAATT TGCTGGGCAT GGTGGTGGGC ACCTGTAATC CCAGGAGGCT    1645
GAGGCAGGAG AATCACTTGA ACCTGGGAGC GGAGATTGCA GTGAGCCAAG ATTGTGCCAT    1705
TGAACTCCAG CCTGGGTGAC AAGACCAAAA CTCCATCTCA AAAAAAAAA AAAAAAAGC      1765
GACAGCAACG G                                                        1776
```

( 2 ) INFORMATION FOR SEQ ID NO:2:

( i ) SEQUENCE CHARACTERISTICS:
        ( A ) LENGTH: 360 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Glu Ser Ile Phe His Glu Lys Gln Glu Gly Ser Leu Cys Ala Gln
 1               5                  10                  15

His Cys Leu Asn Asn Leu Leu Gln Gly Glu Tyr Phe Ser Pro Val Glu
                20                  25                  30

Leu Ser Ser Ile Ala His Gln Leu Asp Glu Glu Arg Met Arg Met
                35                  40                  45

Ala Glu Gly Gly Val Thr Ser Glu Asp Tyr Arg Thr Phe Leu Gln Gln
     50                  55                  60

Pro Ser Gly Asn Met Asp Asp Ser Gly Phe Phe Ser Ile Gln Val Ile
 65                  70                  75                  80

Ser Asn Ala Leu Lys Val Trp Gly Leu Glu Leu Ile Leu Phe Asn Ser
                 85                  90                  95

Pro Glu Tyr Gln Arg Leu Arg Ile Asp Pro Ile Asn Glu Arg Ser Phe
                100                 105                 110

Ile Cys Asn Tyr Lys Glu His Trp Phe Thr Val Arg Lys Leu Gly Lys
                115                 120                 125

Gln Trp Phe Asn Leu Asn Ser Leu Leu Thr Gly Pro Glu Leu Ile Ser
    130                 135                 140

Asp Thr Tyr Leu Ala Leu Phe Leu Ala Gln Leu Gln Gln Glu Gly Tyr
145                 150                 155                 160

Ser Ile Phe Val Val Lys Gly Asp Leu Pro Asp Cys Glu Ala Asp Gln
                165                 170                 175

Leu Leu Gln Met Ile Arg Val Gln Gln Met His Arg Pro Lys Leu Ile
                180                 185                 190

Gly Glu Glu Leu Ala Gln Leu Lys Glu Gln Arg Val His Lys Thr Asp
                195                 200                 205
```

| | | | | | | | | | | | | | | |
|---|---|---|---|---|---|---|---|---|---|---|---|---|---|---|
| Leu | Glu | Arg | Met | Leu | Glu | Ala | Asn | Asp | Gly | Ser | Gly | Met | Leu | Asp | Glu |
| | 210 | | | | 215 | | | | | 220 | | | | | |
| Asp | Glu | Glu | Asp | Leu | Gln | Arg | Ala | Leu | Ala | Leu | Ser | Arg | Gln | Glu | Ile |
| 225 | | | | | 230 | | | | | 235 | | | | | 240 |
| Asp | Met | Glu | Asp | Glu | Glu | Ala | Asp | Leu | Arg | Arg | Ala | Ile | Gln | Leu | Ser |
| | | | | 245 | | | | | 250 | | | | | 255 | |
| Met | Gln | Gly | Ser | Ser | Arg | Asn | Ile | Ser | Gln | Asp | Met | Thr | Gln | Thr | Ser |
| | | | 260 | | | | | 265 | | | | | 270 | | |
| Gly | Thr | Asn | Leu | Thr | Ser | Glu | Glu | Leu | Arg | Lys | Arg | Arg | Glu | Ala | Tyr |
| | | 275 | | | | | 280 | | | | | 285 | | | |
| Phe | Glu | Lys | Gln | Gln | Gln | Lys | Gln | Gln | Gln | Gln | Gln | Gln | Gln | Gln | Gln |
| | 290 | | | | | 295 | | | | | 300 | | | | |
| Gln | Gln | Gln | Gln | Gln | Gln | Gln | Gln | Gln | Gln | Gln | Gln | Arg | Asp | Leu | |
| 305 | | | | | 310 | | | | | 315 | | | | | 320 |
| Ser | Gly | Gln | Ser | Ser | His | Pro | Cys | Glu | Arg | Pro | Ala | Thr | Ser | Ser | Gly |
| | | | | 325 | | | | | 330 | | | | | 335 | |
| Ala | Leu | Gly | Ser | Asp | Leu | Gly | Lys | Ala | Cys | Ser | Pro | Phe | Ile | Met | Phe |
| | | | | 340 | | | | | 345 | | | | | 350 | |
| Ala | Thr | Phe | Thr | Leu | Tyr | Leu | Thr | | | | | | | | |
| | | 355 | | | | | 360 | | | | | | | | |

( 2 ) INFORMATION FOR SEQ ID NO:3:

( i ) SEQUENCE CHARACTERISTICS:
        ( A ) LENGTH: 325 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 145

( i x ) FEATURE:
        ( A ) NAME/KEY: modified_base
        ( B ) LOCATION: 194

( x i ) SEQUENCE DESCRIPTION: SEQ ID NO:3:

| | | | | | |
|---|---|---|---|---|---|
| CTTTTAATAC CAGTGACTAC TTTGATTCGT GAAACAATGT ATTTTCCTTA TGAATAGTTT | | | | | 60 |
| TTCTCATGGT GTATTTATTC TTTTAAGTTT TGTTTTTTAA ATATACTTCA CTTTTGAATG | | | | | 120 |
| TTTCAGACAG CAGCAAAAGC AGCARCAGCA GCAGCAGCAG CAGCAGCAGC AGCAGCAGCA | | | | | 180 |
| GCAGCAGCAG CAGSGGGACC TATCAGGACA GAGTTCACAT CCATGTGAAA GGCCAGCCAC | | | | | 240 |
| CAGTTCAGGA GCACTTGGAA GTGATCTAGG TAAGGCCTGC TCACCATTCA TCATGTTCGC | | | | | 300 |
| TACCTTCACA CTTTATCTGA CATAA | | | | | 325 |

( 2 ) INFORMATION FOR SEQ ID NO:4:

( i ) SEQUENCE CHARACTERISTICS:
        ( A ) LENGTH: 291 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
| Met | Glu | Ser | Ile | Phe | His | Glu | Lys | Gln | Glu | Gly | Ser | Leu | Cys | Ala | Gln |
| 1 | | | | 5 | | | | | 10 | | | | | 15 | |
| His | Cys | Leu | Asn | Asn | Leu | Leu | Gln | Gly | Glu | Tyr | Phe | Ser | Pro | Val | Glu |
| | | | 20 | | | | | 25 | | | | | 30 | | |

```
           Leu  Ser  Ser  Ile  Ala  His  Gln  Leu  Asp  Glu  Glu  Arg  Met  Arg  Met
                     35                  40                      45

Ala  Glu  Gly  Gly  Val  Thr  Ser  Glu  Asp  Tyr  Arg  Thr  Phe  Leu  Gln  Gln
                50                       55                      60

Pro  Ser  Gly  Asn  Met  Asp  Asp  Ser  Gly  Phe  Phe  Ser  Ile  Gln  Val  Ile
           65                       70                  75                           80

Ser  Asn  Ala  Leu  Lys  Val  Trp  Gly  Leu  Glu  Leu  Ile  Leu  Phe  Asn  Ser
                          85                       90                           95

Pro  Glu  Tyr  Gln  Arg  Leu  Arg  Ile  Asp  Pro  Ile  Asn  Glu  Arg  Ser  Phe
                          100                      105                     110

Ile  Cys  Asn  Tyr  Lys  Glu  His  Trp  Phe  Thr  Val  Arg  Lys  Leu  Gly  Lys
                     115                      120                     125

Gln  Trp  Phe  Asn  Leu  Asn  Ser  Leu  Leu  Thr  Gly  Pro  Glu  Leu  Ile  Ser
                130                      135                     140

Asp  Thr  Tyr  Leu  Ala  Leu  Phe  Leu  Ala  Gln  Leu  Gln  Gln  Glu  Gly  Tyr
           145                      150                     155                          160

Ser  Ile  Phe  Val  Val  Lys  Gly  Asp  Leu  Pro  Asp  Cys  Glu  Ala  Asp  Gln
                               165                     170                     175

Leu  Leu  Gln  Met  Ile  Arg  Val  Gln  Gln  Met  His  Arg  Pro  Lys  Leu  Ile
                          180                      185                     190

Gly  Glu  Glu  Leu  Ala  Gln  Leu  Lys  Glu  Gln  Arg  Val  His  Lys  Thr  Asp
                          195                      200                     205

Leu  Glu  Arg  Met  Leu  Glu  Ala  Asn  Asp  Gly  Ser  Gly  Met  Leu  Asp  Glu
                          210                      215                     220

Asp  Glu  Glu  Asp  Leu  Gln  Arg  Ala  Leu  Ala  Leu  Ser  Arg  Gln  Glu  Ile
           225                           230                     235                     240

Asp  Met  Glu  Asp  Glu  Glu  Ala  Asp  Leu  Arg  Arg  Ala  Ile  Gln  Leu  Ser
                               245                     250                     255

Met  Gln  Gly  Ser  Ser  Arg  Asn  Ile  Ser  Gln  Asp  Met  Thr  Gln  Thr  Ser
                          260                      265                     270

Gly  Thr  Asn  Leu  Thr  Ser  Glu  Glu  Leu  Arg  Lys  Arg  Arg  Glu  Ala  Tyr
                     275                      280                     285

Phe  Glu  Lys
                     290
```

( 2 ) INFORMATION FOR SEQ ID NO:5:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:5:

```
           Arg  Asp  Leu  Ser  Gly  Gln  Ser  Ser  His  Pro  Cys  Glu  Arg  Pro  Ala  Thr
           1                   5                   10                      15

Ser  Ser  Gly  Ala  Leu  Gly  Ser  Asp  Leu  Gly  Lys  Ala  Cys  Ser  Pro  Phe
                          20                      25                      30

Ile  Met  Phe  Ala  Thr  Phe  Thr  Leu  Tyr  Leu  Thr
                     35                      40
```

( 2 ) INFORMATION FOR SEQ ID NO:6:

( i ) SEQUENCE CHARACTERISTICS:
        ( A ) LENGTH: 873 base pairs
        ( B ) TYPE: nucleic acid (C) STRANDEDNESS: single
(D) TOPOLOGY: linear (i i) MOLECULE TYPE: DNA (genomic)

(x i) SEQUENCE DESCRIPTION: SEQ ID NO:6:

| | | | | | | |
|---|---|---|---|---|---|---|
| ATGGAGTCCA | TCTTCCACGA | GAAACAAGAA | GGCTCACTTT | GTGCTCAACA | TTGCCTGAAT | 60 |
| AACTTATTGC | AAGGAGAATA | TTTTAGCCCT | GTGGAATTAT | CCTCAATTGC | ACATCAGCTG | 120 |
| GATGAGGAGG | AGAGGATGAG | AATGGCAGAA | GGAGGAGTTA | CTAGTGAAGA | TTATCGCACG | 180 |
| TTTTTACAGC | AGCCTTCTGG | AAATATGGAT | GACAGTGGTT | TTTTCTCTAT | TCAGGTTATA | 240 |
| AGCAATGCCT | TGAAAGTTTG | GGGTTTAGAA | CTAATCCTGT | TCAACAGTCC | AGAGTATCAG | 300 |
| AGGCTCAGGA | TCGATCCTAT | AAATGAAAGA | TCATTTATAT | GCAATTATAA | GGAACACTGG | 360 |
| TTTACAGTTA | GAAAATTAGG | AAAACAGTGG | TTTAACTTGA | ATTCTCTCTT | GACGGGTCCA | 420 |
| GAATTAATAT | CAGATACATA | TCTTGCACTT | TTCTTGGCTC | AATTACAACA | GGAAGGTTAT | 480 |
| TCTATATTTG | TTGTTAAGGG | TGATCTGCCA | GATTGCGAAG | CTGACCAACT | CCTGCAGATG | 540 |
| ATTAGGGTCC | AACAGATGCA | TCGACCAAAA | CTTATTGGAG | AAGAATTAGC | ACAACTAAAA | 600 |
| GAGCAAAGAG | TCCATAAAAC | AGACCTGGAA | CGAATGTGAG | AAGCAAATGA | TGGCTCAGGA | 660 |
| ATGTTAGACG | AAGATGAGGA | GGATTTGCAG | AGGGCTCTGG | CACTAAGTCG | CCAAGAAATT | 720 |
| GACATGGAAG | ATGAGGAAGC | GAATCTCCGC | AGGGCTATTC | AGCTAAGTAT | GCAAGGTAGT | 780 |
| TCCAGAAACA | TATCTCAAGA | TATGACACAG | ACATCAGGTA | CAAATCTTAC | TTCAGAAGAG | 840 |
| CTTCGGAAGA | GACGAGAAGC | CTACTTTGAA | AAA | | | 873 |

(2) INFORMATION FOR SEQ ID NO:7:

(i) SEQUENCE CHARACTERISTICS:
(A) LENGTH: 129 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:7:

| | | | | | | |
|---|---|---|---|---|---|---|
| CGGGACCTAT | CAGGACAGAG | TTCACATCCA | TGTGAAAGGC | CAGCCACCAG | TTCAGGAGCA | 60 |
| CTTGGGAGTG | ATCTAGGTAA | GGCCTGCTCA | CCATTCATCA | TGTTCGCTAC | CTTCACACTT | 120 |
| TATCTGACA | | | | | | 129 |

(2) INFORMATION FOR SEQ ID NO:8:

(i) SEQUENCE CHARACTERISTICS:
(A) LENGTH: 925 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:8:

| | | | | | | |
|---|---|---|---|---|---|---|
| GAATTCCGTT | GCTGTCGTCG | GCGTGGGGGC | CGTTGGCTCC | AGACAAATAA | ACATGGAGTC | 60 |
| CATCTTCCAC | GAGAAACAAG | AAGGCTCACT | TTGTGCTCAA | CATTGCCTGA | ATAACTTATT | 120 |
| GCAAGGAGAA | TATTTTAGCC | CTGTGGAATT | ATCCTCAATT | GCACATCAGC | TGGATGAGGA | 180 |
| GGAGAGGATG | AGAATGGCAG | AAGGAGGAGT | TACTAGGGAA | GATTATCGCA | CGGTGTGACA | 240 |
| GCAGCCTTCT | GGAAATATGG | ATGACAGTGG | TTTTTTCTCT | ATTCAGGTTA | TAAGCAATGC | 300 |
| CTTGAAAGTT | TGGGGTTTAG | AACTAATCCT | GTTCAACAGT | CCAGAGTATC | AGAGGCTTAG | 360 |

```
GATCGATCCT ATAAATGAAA GATCATTTAT ATGCAATTAT AAGGAACACT GGTTTACAGT      420

TAGAAAATTA GGAAAACAGT GGTTTAACTT GAATTCTCTC TTGACGGGTC CAGAATTAAT      480

ATCAGATACA TATCTTGCAC TTTTCTTGGC TCAATTACAA CAGGAAGGTT ATTCTATATT      540

TGTTGTTAAG GGTGATCTGC CAGATTGCGA AGCTGACCAA CTCCTGCAGA TGATTAGGGT      600

CCAACAGATG CATCGACCAA AACTTATTGG AGAAGAATTA GCACAACTAA AAGAGCAAAG      660

AGGCCATAAA ACAGACCTGG AACGAATGTT AGAAGCAAAT GATGGCTCAG GAATGTTAGA      720

CGAAGATGAG GAGGATTTGC AGAGGGCTCT GGCACTAAGT CGCCAAGAAA TTGACATGGA      780

AGATGAGGAA GCAGATCTCC GCAGGGCTAT TCAGCTAAGT ATGCAAGGTA GTTCCAGAAA      840

CATATCTCAA GATATGACAC AGACATCAGG TACAAATCTT ACTTCAGAAG AGCTTCGGAA      900

GAGACGAGAA GCCTACTTTG AAAAA                                            925
```

( 2 ) INFORMATION FOR SEQ ID NO:9:

( i ) SEQUENCE CHARACTERISTICS:
        ( A ) LENGTH: 807 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

```
CGGGACCTAT CAGGACAGAG TTCACATCCA TGTGAAAGGC CAGCCACCAG TTCAGGAGCA       60

CTTGGGAGTG ATCTAGGTAA GGCCTGCTCA CCATTCATCA TGTTCGCTAC CTTCACACTT      120

TATCTGACAT AAGAGCTCCA TGTGATTTTT GCTTTACATT ATTCTTCATT CCCTCTTTAA      180

TCATATTAAG ACTCTTAAGT AAATTTGAAT CTACTAAATT TCCCTGGATT AAGGAGCAAG      240

GGTACCAAAA AAAAAAAAAA AAAAAAAAGC TAGATGTGGT GGCTCACATC TGTAATCCCA      300

GCACTTTGGG AAACCAAGGC AGGAGAGGAT TGCTAGAACA TTTAATGAAT ACTTTAACAT      360

AATAATTTAA ACTTCACAGT AATTTGTACA GTCTCCAGAA ATTCCTTAGA CATCATGAAT      420

ATTTTTCTTT TTTTGGGGTG ACAGGGCAAA ACTCTGTCTC AAAAAAAAAA AAAAAAAAA      480

AAGGGCTGGA CACGGTGGCT TACGCCTGTT ATCCCGGCAC TTTGGGAGGC CAAGGCCGAT      540

GGATCACCTG AGGTCAGGAG TTCAAGACCA GCCTGGCCAA CATGGTGAAA CCCCATCTCT      600

ACTAAAAATA CAAAAATTTG CTGGGCATGG TGGTGGGCAC CTGGAATCCC AGGAGGCTGA      660

GGCAGGAGAA TCACTTGAAC CTGGGAGCGG AGATTGCAGT GAGCCAAGAT TGTGCCATTG      720

AACTCCAGCC TGGGTGACAA GACCAAAACT CCATCTCAAA AAAAAAAAA AAAAAAGGGG      780

ACAGCAACGG CGACAGCAAC GGAATTC                                          807
```

( 2 ) INFORMATION FOR SEQ ID NO:10:

( i ) SEQUENCE CHARACTERISTICS:
        ( A ) LENGTH: 128 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

```
CTTTTAATAC CAGTGACTAC TTTGATTCGT GAAACAATGT ATTTTCCTTA TGAATAGTTT       60

TTCTCCATGG TGTATTTATT CTTTTAAGTT TTGTTTTTTA AATATACTTC ACCTTTTGAA      120

TGTTCAGA                                                               128
```

( 2 ) INFORMATION FOR SEQ ID NO:11:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

```
CGGGACCTAT  CAGGACAGAG  TTCACATCCA  TGTGAAAGGC  CAGCCACCAG  TTCAGGAGCA      60
CTTGGGAGTG  ATCTAG                                                          76
```

( 2 ) INFORMATION FOR SEQ ID NO:12:

( i ) SEQUENCE CHARACTERISTICS:
        ( A ) LENGTH: 128 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

```
CTTTTAATAC  CAGTGACTAC  TTTGATTCGT  GAAACAATGT  ATTTTCCTTA  TGAATAGTTT      60
TTCTCCATGG  TGTATTTATT  CTTTTAAGTT  TTGTTTTTTA  AATATACTTC  ACCTTTTGAA     120
TGTTTCAG                                                                   128
```

( 2 ) INFORMATION FOR SEQ ID NO:13:

( i ) SEQUENCE CHARACTERISTICS:
        ( A ) LENGTH: 129 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

```
CGGGACCTAT  CAGGACAGAG  TTCACATCCA  TGTGAAAGGC  CAGCCACCAG  TTCAGGAGCA      60
CTTGGGAGTG  ATCTAGGTAA  GGCCTGCTCA  CCATTCATCA  TGTTCGCTAC  CTTCACACTT     120
TATCTGACA                                                                  129
```

( 2 ) INFORMATION FOR SEQ ID NO:14:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

```
CCAGTGACTA  CTTTGATTCG                                                      20
```

( 2 ) INFORMATION FOR SEQ ID NO:15:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear (i i) MOLECULE TYPE: DNA (genomic)

(x i) SEQUENCE DESCRIPTION: SEQ ID NO:15:

TGGCCTTTCA CATGGATGTG AA    22

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:16:

CTTACCTAGA TCACTCCCAA    20

(2) INFORMATION FOR SEQ ID NO:17:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:17:

GATCTCTGCT GCTGCTGCTG CTGCTGGCTG CTGCTGCTGC TGG    43

(2) INFORMATION FOR SEQ ID NO:18:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:18:

TCTTACTTCA GAAGAGCTTC GGAAG    25

(2) INFORMATION FOR SEQ ID NO:19:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:19:

GCTGGCCTTT CACATGGATG TGAAC    25

(2) INFORMATION FOR SEQ ID NO:20:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:20:

ACGAGAAGCC TACTTTGA    18

(2) INFORMATION FOR SEQ ID NO:21:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:21:

AACTCTGTCC TGATAGGT                                                    18

(2) INFORMATION FOR SEQ ID NO:22:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:22:

TCGTGAAACA ATGTATTTTC CTTATG                                           26

(2) INFORMATION FOR SEQ ID NO:23:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:23:

GATGTGAACT CTGTCCTGAT                                                  20